United States Patent
Lewis et al.

(10) Patent No.: US 12,065,660 B2
(45) Date of Patent: Aug. 20, 2024

(54) TRANSGENIC SILKWORMS EXPRESSING HAGFISH THREAD KERATIN

(71) Applicant: Utah State University, North Logan, UT (US)

(72) Inventors: Randolph V. Lewis, Nibley, UT (US); Justin A. Jones, Nibley, UT (US); Xiaoli Zhang, Nibley, UT (US)

(73) Assignee: UTAH STATE UNIVERSITY, North Logan, UT (US)

( * ) Notice: Subject to any disclaimer, the term of this patent is extended or adjusted under 35 U.S.C. 154(b) by 665 days.

(21) Appl. No.: 16/995,372

(22) Filed: Aug. 17, 2020

(65) Prior Publication Data
US 2021/0047655 A1    Feb. 18, 2021

Related U.S. Application Data

(60) Provisional application No. 62/888,284, filed on Aug. 16, 2019.

(51) Int. Cl.
*C12N 15/85* (2006.01)
*C07K 14/46* (2006.01)
*C07K 14/78* (2006.01)

(52) U.S. Cl.
CPC ........ *C12N 15/8509* (2013.01); *C07K 14/461* (2013.01); *C07K 14/78* (2013.01); *A01K 2217/07* (2013.01); *A01K 2227/706* (2013.01)

(58) Field of Classification Search
CPC .................................................. C12N 15/8509
See application file for complete search history.

(56) References Cited

FOREIGN PATENT DOCUMENTS

KR        101419033        7/2014
WO        2003069033 A1    8/2003

OTHER PUBLICATIONS

Lewis et al. (2002, Molecular Biology of the Cell, 4th Ed., Garland Science, pp. 1-24) (Year: 2002).*
Burga et al., 2012, FEBS J., vol. 279, pp. 3765-3775 (Year: 2012).*
Fu, J., et al., "Self-Assembly of recombinant hagfish thread keratins amenable to a strain-induced alpha-helix to beta-sheet transition", Biomacromolecules (2015), vol. 16, pp. 2327-2339.
Fu, J., et al., "Artificial hagfish protein fibers with ultra-high tunable stiffness", Nanoscale (2017), vol. 9, pp. 12908-12915.

\* cited by examiner

*Primary Examiner* — Anoop K Singh
*Assistant Examiner* — David A Montanari
(74) *Attorney, Agent, or Firm* — Ryan L. Marshall; Barnes & Thornburg LLP

(57) ABSTRACT

Transgenic silkworms stably expressing hagfish thread keratin genes or composite silkworm/hagfish thread keratin genes are disclosed. The exogenous hagfish thread keratin genes are stably integrated into a defined site of the fibroin heavy chain intron or a fibroin light chain intron of silkworms. Synthetic hagfish thread keratin proteins and composite hagfish thread keratin-silkworm genes and proteins are provided. The expression of exogenous hagfish thread keratin genes is driven by the endogenous fibroin heavy chain promoter, improving the genetic stability of transgenic silkworms. The composite silkworm/hagfish thread keratin fibers exhibit exceptional mechanical performance, compared to normal silkworm silk fibers and other transgenic silkworm fibers.

10 Claims, 7 Drawing Sheets

Specification includes a Sequence Listing.

TRANSGENIC SILKWORMS EXPRESSING HAGFISH THREAD KERATIN

CROSS-REFERENCE TO RELATED APPLICATIONS

This application is a U.S. Non-provisional application claiming priority under 35 U.S.C. 120 and 119(e) to U.S. provisional application No. 62/888,284, filed Aug. 16, 2019. The disclosure of this priority application is incorporated herein in its entirety.

GOVERNMENT LICENSE RIGHTS

This invention was made with government support under award number N61331-20-D0001, awarded by the Office of Naval Research. The government has certain rights in the invention.

REFERENCE TO SEQUENCE LISTING

A sequence listing entitled "323182_Sequence_listing_ST25" is an ASCII text file and is incorporated herein by reference in its entirety. The text file was created on Jul. 25, 2020 and is 109.5 KB in size.

BACKGROUND

1. Field of the Invention

The present disclosure relates to transgenic silkworms. More specifically, the disclosure relates to transgenic silkworms that express hagfish thread keratin proteins. Also disclosed are the nucleic acid sequences used to express those proteins and methods for producing such silkworms, including methods utilizing an optimized CRISPR/Cas9 system.

2. Description of the Related Art

Hagfish slime is an intriguing biomaterial that protects hagfish from predation. The slime is ejected from specialized gland mucus cells and rapidly swells when exposed to seawater. The slime is composed of thread keratins (TK's) and a mucin like component. As marine predators suck the hagfish into their mouth the, slime coats their gills causing them to expel the hagfish.

Hagfish thread keratins are comprised of two subunits, alpha and gamma ($\alpha$ and $\gamma$). When produced in the hagfish, they form a coiled coil of helices that when strained convert to $\beta$-sheets. They are expressed and form a fiber in a different manner than both spider and silkworm silk. As the growing peptide chain is produced from the ribosome, it assembles without the need for associated mechanisms of storage as is the case for both spider silk and silkworm silk. The $\alpha$ and $\gamma$ strands of proteins are helical, and they then coil around each other in a coiled-coil conformation. This conformation is challenging to reproduce synthetically.

Thread keratins (TK) have intriguing mechanical properties. The TK's are stored in specialized invaginations in the skin of the hagfish and coiled into a readily deployable, non-knotting, football like shape. When ejected along with the concentrated slime, the fiber elongates and acts to reinforce the slime. The fibers can be finer than spider silk with reported mechanical properties that are 10×'s that of nylon and rival that of spider silk. These properties make the hagfish TK's a desirable biomaterial. Given that farming hagfish for their slime is impractical and producing the hagfish TK's in their native cells is not currently possible, other hosts have been explored. While the sequences have been known for some time, there are almost no reports in the literature of them being expressed in a heterologous host (*E. coli*) and spun into fibers (Jing Fu, et al., *Biomacromolecules* 2015, 16, 8, 2327-2339; Jing Fu et al., *Nanoscale,* 2017, 9, 12908-12915).

Synthetic TK's are problematic when produced in *E. coli*. These proteins are expressed and accumulate in the insoluble fraction. This necessitates difficult purification strategies and a process to dissolve the proteins, fold them correctly in their native individual conformations, and then combine both $\alpha$ and $\gamma$ proteins and again fold them correctly into their final coiled-coil structure. The combined proteins must then be formed into a fiber. The result is that fibers formed from these thread keratins currently have not performed up to their native counterparts mechanical ability. The approach of utilizing common *E. coli* to produce the proteins is fraught with technological challenges and shortcomings as it is not remotely mimetic to the way nature produces the thread keratin fibers in the hagfish.

BRIEF SUMMARY

A transgenic silkworm is disclosed that includes an exogenous hagfish thread keratin gene operably linked to an endogenous silkworm promoter.

A progeny silkworm of the transgenic silkworm disclosed herein is provided. The exogenous hagfish thread keratin gene may be stably integrated in the silkworm progeny.

A transgenic silkworm (*Bombyx mori*) is provided. The silkworm may include a stably-integrated hagfish thread keratin gene in the sixth intron of the fibroin light chain gene FibL or a first intron of the fibroin heavy chain gene, FibH and operably linked to the endogenous fibroin light promoter or the endogenous fibroin heavy promoter. The transgenic silkworm may stably express the hagfish thread keratin gene.

A composition is provided that may include a hagfish thread keratin protein and silkworm protein.

A vector is provided that may include an isolated nucleic acid that encodes a hagfish thread keratin gene.

A method for producing a transgenic silkworm is provided. The method may include introducing a hagfish thread keratin gene into a defined site of the silkworm genome using a CRISPR/Cas9 system, such that the hagfish thread keratin gene is operably linked to an endogenous silkworm promoter. The exogenous nucleic acid may be stably integrated into the silkworm genome.

A method for producing a hagfish thread keratin protein is provided. The method may include introducing an isolated nucleic acid comprising SEQ ID NO: 1, SEQ ID NO: 47, SEQ ID NO: 48, or SEQ ID NO: 2, or a fragment of either thereof, into a defined site in the genome of a silkworm. The isolated nucleic acid may be stably integrated into the silkworm genome; expressing the exogenous nucleic acid under control of an endogenous promoter; and isolating hagfish thread keratin protein from the silkworm.

The foregoing broadly outlines the features and technical advantages of the present disclosure in order that the detailed description that follows may be better understood. Additional features and advantages of the disclosure will be described hereinafter that form the subject of the claims of this application. It will be appreciated by those of skill in the art that the conception and specific aspects disclosed herein may be readily utilized as a basis for modifying or designing other aspects for carrying out the same purposes of the present disclosure within the spirit and scope of the disclosure and provided in the appended claims.

BRIEF DESCRIPTION OF THE SEVERAL VIEWS OF THE DRAWINGS

A detailed description of the invention is hereafter provided with specific reference being made to the drawings in which.

DETAILED DESCRIPTION

Figure 1:
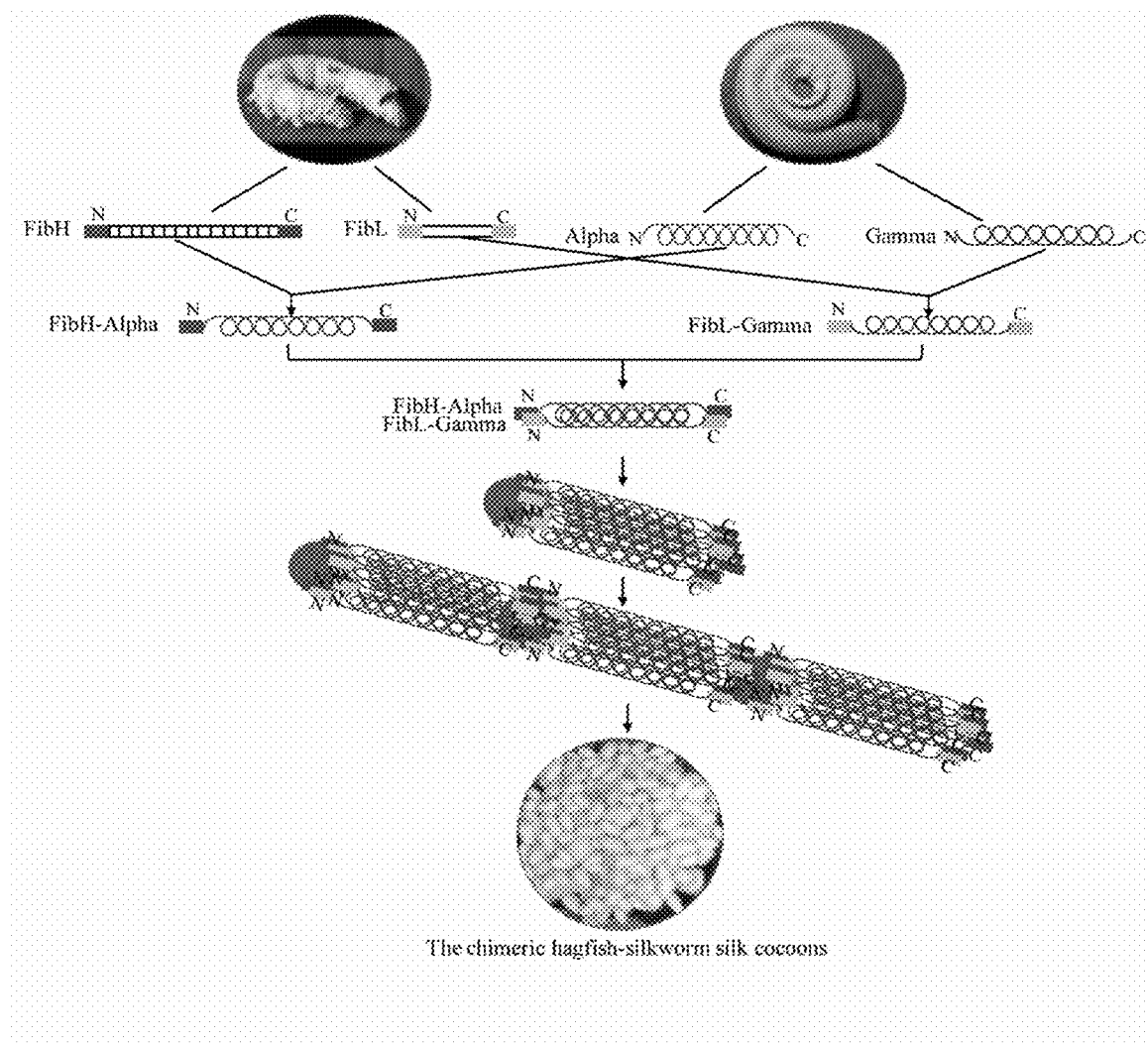
FIG. 1 illustrates an embodiment of the present application where the hagfish thread keratin alpha is incorporated into the fibroin heavy chain of the silkworm and hagfish thread keratin gamma is incorporated into the fibroin light chain of the silkworm.

Various aspects are described below with reference to the drawings. The relationship and functioning of the various elements of the aspects may better be understood by reference to the following detailed description. However, aspects are not limited to those illustrated in the drawings or explicitly described below. It should be understood that the drawings are not necessarily to scale, and in certain instances details may have been omitted that are not necessary for an understanding of aspects disclosed herein, such as conventional fabrication and assembly. Headings are provided for the convenience of the reader and to assist organization of the disclosure and should not be construed to limit or otherwise define the scope of the invention.

The silkworm *Bombyx mori* or *Bombyx mandarina* can be used as a platform for producing recombinant silkworm/spider silk fibers. *B. mori* has a similar natural fiber spinning process to that of spiders, is a prolific silk producer, and can be farmed commercially. In some aspects, therefore, the silkworm is *Bombyx mori*.

In the silk gland, micellar-like structures are formed because of the aggregation of the silk proteins under a remarkably high concentration, and then β-sheet crystals are formed due to shear forces imposed as the protein liquid flows along the duct. The protein structure in the fiber occurs as the fiber is pulled out of the spigot of the spider or the mouth of the silkworm, further increasing the shear stress.

In one aspect, the disclosure provides transgenic silkworms stably expressing hagfish thread keratin genes or composite hagfish thread keratin-silkworm genes.

As used herein, the term "hagfish thread keratin gene" is understood to include a gene sequence or resulting gene expression product (e.g., protein) that encompasses some or all of the native gene sequence or gene expression product, but is removed or otherwise isolated from its native host. As such, a "hagfish thread keratin gene" is understood to include a DNA sequence that has at least 70%, at least 75%, at least 80%, at least 85%, at least 90%, at least 95%, at least 96%, at least 97%, at least 98%, at least 99%, or 100% sequence identity with the native hagfish thread keratin gene over at least a 20 base pair (bp) contiguous segment of the gene or that produces a gene expression product having at least at least 70%, at least 75%, at least 80%, at least 85%, at least 90%, at least 95%, at least 96%, at least 97%, at least 98%, at least 99%, or 100% protein sequence identity with the native hagfish thread keratin protein over at least a 20 amino acid contiguous segment of the protein. The hagfish thread keratin gene can be referred to as a synthetic gene. The term "synthetic" may be used herein interchangeably with the terms "exogenous" or "transgenic," particularly when describing a synthetic gene sequence that is derived from an organism different from its current host.

In some aspects, transgenically-produced hagfish thread keratin or composite hagfish thread keratin-silkworm silk reflects about 10-15% of the total silk production by the silkworm. In other aspects, transgenically-produced hagfish thread keratin or composite hagfish thread keratin-silkworm silk reflects over 15%, over 20%, over 25%, over 30%, over 35%, over 40%, over 45%, over 50%, over 55%, over 60%, over 65%, over 70%, over 75%, over 80%, over 85%, over 90%, over 95%, over 99%, or about 100% of the total silk production by the silkworm.

In this respect, the engineered hagfish thread keratin may substantially replace endogenous production of one or more of the silkworm's own silk-associated proteins, such as the silkworm fibroin protein.

It is understood that the protein fibroin, including the fibroin heavy chain and fibroin light chain, is the core protein component of silk in silkworms. Thus, the terms "fibroin" or "silk protein" may in some cases be used interchangeably herein with reference to "silk," as appropriate.

The limitations of prior technology have made it difficult to produce transgenic silkworms that stably integrate a transgene larger than about 3 kb in length in silkworms. In some aspects, a transgenic silkworm is disclosed, the transgenic silkworm having a stably-integrated hagfish thread keratin gene. In some aspects, the hagfish thread keratin gene may be greater than about three kilobases (3 kb) in length. In certain embodiments, the stably-integrated hagfish thread keratin gene is greater than about 4 kb in length; greater than about 5 kb in length; or greater than about 6 kb in length.

As used herein, the term "stably integrated" means that the introduced transgenic material is capable of successfully passing through cell division to daughter cells and/or offspring, for example, into the second generation, third generation, etc., without substantial change in sequence or the transgenic material being lost. Thus, in some aspects, a stably integrated transgene is present in the first generation, second generation, third generation, etc. of a transgenic silkworm (i.e., in progeny). In certain aspects, the stably integrated transgene is expressed in the first generation, second generation, third generation, etc. of a transgenic silkworm (i.e., in progeny).

It is also understood that stable integration of an exogenous nucleotide sequence into a host gene, such as through a CRISPR/Cas9 mediated knock-in system, may produce a composite (i.e., hybrid) gene including both exogenous and endogenous nucleic material. Thus, in some aspects, a transgenic silkworm is disclosed, the transgenic silkworm having a composite hagfish thread keratin-silkworm gene.

It is further understood that expression of such a composite gene sequence may produce a composite (i.e., hybrid or fusion) protein or proteins. Thus, in some aspects, a transgenic silkworm is disclosed that stably expresses a hagfish thread keratin gene or a composite/hybrid hagfish thread keratin-silkworm gene.

In embodiments, integrated genes are expressed under control (i.e., operably linked) of an endogenous promoter in the silkworms. In some aspects, a hagfish thread keratin gene is operably linked to an endogenous promoter. For example, exogenous hagfish genetic material may be introduced into the single intron of the silkworm fibroin heavy chain gene, FibH, with stable expression of the integrated transgene driven by an endogenous promoter. In another example, exogenous hagfish genetic material may be introduced into any of the six introns of the silkworm fibroin light chain gene, FibL, with stable expression of the integrated transgene driven by an endogenous promoter. Expression of *Eptatretus stoutii* thread keratin α or *Eptatretus stoutii* thread keratin γ in silkworm, driven by an endogenous fibroin promoter, appears to improve genetic stability in transgenic silkworms. In specific aspects, the endogenous silkworm promoter is the silkworm-specific FibH or FibL promoter.

In some aspects, the exogenous hagfish thread keratin gene may comprise the *Eptatretus stoutii* thread keratin α gene (SEQ ID NO: 1 or SEQ ID NO: 47), *Eptatretus stoutii* thread keratin γ (SEQ ID NO: 2 or SEQ ID NO: 48), or synthetic variants thereof.

The disclosed hybrid proteins may be larger and more stable than previous transgenic silk proteins. In embodiments, the transgenic hagfish thread keratin proteins and/or composite hagfish thread keratin-silkworm silk proteins have mechanical properties comparable to or superior to natural hagfish thread keratin.

A silk composition is provided that may include a hagfish thread keratin proteins and/or composite hagfish thread keratin-silkworm silk proteins. In other aspects, a vector is provided that may include a hagfish thread keratin gene operably linked to an endogenous silkworm promoter.

In one aspect, methods are disclosed for producing transgenic silkworms. Current genome editing technologies facilitate introducing site-specific modifications in the genomes of cells and organisms and provide a means to deliver exogenous genes at precise target sites in silkworms. Preliminary applications of the latest genomic editing technologies such as zinc-finger nucleases (ZFN), transcription activator-like effector nucleases (TALENs), and the clustered regularly interspaced short palindromic repeat (CRISPR) system in silkworms have mostly focused on the silkworm phenotype gene (BmBLOS2) or the non-phenotype gene (Bmku70). For example, researchers disrupted the fibroin heavy chain (FibH) gene of silkworm glands using a customized ZFN. Applications of these genome editing techniques in silkworms are generally limited to the knock-out phase, however.

Thus, in some aspects, a hagfish thread keratin gene and/or composite hagfish thread keratin-silkworm silk gene is expressed in the silk gland of a silkworm. In other embodiments, a hagfish thread keratin gene and/or composite hagfish thread keratin-silkworm silk gene is expressed in other tissues or organs of a silkworm.

The CRISPR/Cas9 system has been used in different research models, including insect cells, plants and human cells. The advantages of this system are the relatively easy production and design of constructs, time-saving production of transgenic organisms, and binding stability to the genomic DNA.

CRISPR has two components: a "guide" RNA (gRNA) and a non-specific CRISPR-associated endonuclease (Cas9). CRISPR creates DNA double strand breaks (DSBs) at a defined position in a chromosome. The Cas9-mediated DSBs can be spontaneously repaired via the independent pathway of homology-directed repair (HDR) or non-homologous, end-joining (NHEJ).

The homologous recombination-mediated knock-in system has been the preferred technology to introduce foreign genes into desired hosts. For example, using the CRISPR/Cas9 system, an exogenous DNA fragment has been added through precise and controlled homologous recombination (HR) repair systems in *Caenorhabditis elegans*. One limitation of this approach is that it is difficult to incorporate large DNA fragments into the target organism.

Nonhomologous end-joining (NHEJ), which acts independently of the HR pathway(s), is highly efficient. For example, a 15 kb inducible gene expression cassette has been introduced at a defined locus in human cell lines using NHEJ. But NHEJ is associated with potentially damaging nucleotide insertions and deletions (indels) and/or substitutions in the DSB region, which can reduce transgene stability and expression.

Thus, in some aspects, the CRISPR/Cas9 system employs non-homologous recombination (end-joining) to facilitate introduction of large exogenous nuclear material, while targeting an integration site that is not affected by adjacent mutations.

In some aspects, an optimized CRISPR/Cas9 system is utilized to introduce relatively large hagfish thread keratin genes into silkworm. This strategy overcomes the limitations of random integrations of transposon-based piggyBac system and other systems known in the art, including other applications of CRISPR itself. The disclosed methods facilitate insertion of large exogenous DNA fragments at defined sites within the silkworm genome. In some aspects, fragments of the disclosed hagfish thread keratin genes are introduced into a silkworm.

Methods for introducing the isolated nucleotide include, but are not limited to, physical methods of transfection including electroporation, microinjection and biolistic delivery with a gene gun. Chemical transfection methods may use calcium phosphate co-precipitation, diethylaminoethyl-dextran, or cationic lipid-based transfection reagents.

In a specific embodiment, a method is disclosed for producing a transgenic silkworm, the method comprising: introducing an exogenous hagfish thread keratin gene operably linked to an endogenous silkworm promoter.

In a specific embodiment, a method is disclosed for producing a transgenic silkworm, the method comprising: introducing an isolated nucleic acid having SEQ ID NO: 1, SEQ ID NO: 47, SEQ ID NO: 48, or SEQ ID NO: 2, or a fragment of either thereof, into a defined site of the silkworm genome using a CRISPR/Cas9 system, such that the isolated nucleic acid is operably linked to an endogenous silkworm promoter, wherein the exogenous nucleic acid is stably integrated into the silkworm genome.

In certain aspects, the disclosed methods do not require use of exogenous promoters in the HC/LC-NHEJ donors.

For example, using the methods disclosed herein, two large hagfish thread keratin genes may be successfully integrated at the defined locus of the fibroin heavy/light chain gene using optimized CRISPR/Cas9 initiated non-homologous end joining. The incorporated hagfish thread keratin genes may be fully expressed under the endogenous FibH/FibL promoter of silkworm.

An optimized CRISPR/Cas9 system, as used herein, may be specifically designed for efficient and stable integration and expression of a transgenic sequence in silkworm. In some aspects, the CRISPR/Cas9 system is optimized for silkworms using the silkworm-specific U6 promoter. The CRISPR/Cas9 system may be further optimized by targeting silkworm genomic sequences (e.g., introns) that are not disrupted by introduction of exogenous nucleic acid material.

In certain aspects, relatively large hagfish thread keratin genes are thus successfully integrated into the intron of the FibH gene and/or into an intron of the FibL gene. In some aspects, the hagfish thread keratin α gene may be integrated into the intron of the FibH gene and the hagfish thread keratin γ gene may be integrated into the intron of the FibL gene. In some aspects, the hagfish thread keratin γ gene may be integrated into the intron of the FibH gene and the hagfish thread keratin α gene may be integrated into the intron of the FibL gene. In some aspects, the exogenous hagfish thread keratin gene may be integrated into the first intron of the FibH gene. In some aspects, the exogenous hagfish thread keratin gene may be integrated into the sixth intron of the FibL gene.

The following examples are provided to illustrate certain features and/or aspects of the disclosure. The examples should not be construed to limit the disclosure to the particular features or aspects described therein.

EXAMPLES

Example 1. Hagfish Thread Keratin Transgenes in FibL Intron

An optimized silkworm-specific CRISPR/Cas9 system was used with NHEJ. Expression was driven by the endogenous FibL promoter in the transgenic silkworm glands to improve yields and ensure genetic stability.

Construction of Cas9 and sU6 gRNA Expression Vectors for Silkworm.

To ensure the CRISPR/Cas9 system was well expressed in BmN cells and/or silkworms, the coding region of cas9 was constructed into a pIEx™-1 vector under the hr5 enhancer and IE1 promoter to form the pIEx™-1-Cas9 plasmid.

To construct the expression vector of Cas9 in silkworms, the coding region of Cas9 was excised from Px330-U6-Chimeric BB-CBh-hSpCas9 (Addgene plasmid #42230) with AgeI and NotI (NEB, R3552S and R3189S), gel-purified (Qiagen, No. 28704), recovered and sub-cloned into the corresponding sites downstream of the hr5 enhancer and IE1 promoter in pIEx™-1 (Novagen, No. 71241-3) to form pIEx™-1-Cas9.

This gBlock DNA fragment was PCR-amplified (primer 1: AGGTTATGTAGTACACATTG [SEQ ID NO: 3] and primer 2: TTAATGCCAACTTTGTACA [SEQ ID NO: 4]) and then sub-cloned into the pGEM®-T easy vector system (Promega, A3600) to form pGEM®-T-sU6 (silkworm U6). Oligo gRNAs (gRNA_sU6_FibH_1-3 and gRNA_sU6_FibL_5, 6) having 19-20 nucleotides. See Table 1, below, which shows the gRNAs design of the CRISPR/Cas9 system. Sequences listed in Table 1 labeled gRNA_sU6_FibL_5, 6 are SEQ ID NOS: 5-6, respectively. Sequences listed in Table 1 labeled gRNA_sU6_FibH_1, 2, 3 are SEQ ID NOS: 12, 13, and 14, respectively.

TABLE 1

| Name | Target Sequence | Genome Location |
|---|---|---|
| gRNA_sU6_FibH_1 | GCTAATAGGTAGGGAAAAC | AF226688: 63141-63159 |
| gRNA_sU6_FibH_2 | ATGTGACCATAAAATCTCG | AF226688: 63194-63212 |
| gRNA_sU6_FibH_3 | AACTCGTTCCAGATCAGCGC | AF226688: 63341-63360 |
| gRNA_sU6_FibL_5 (g5) | AGAACTTTAAATTATATCT | M76430.1: 13857-13875 |
| gRNA_sU6_FibL_6 (g6) | TCACTATGAGACTTAAGCT | M76430.1: 13880-13898 |

The oligos, including sgRNA targeting sites and part of sgRNA frame, were also ordered from Integrated DNA Technologies and were annealed and extended to form double strand DNAs. These double strand DNAs were gel-purified (Qiagen, No. 28704) and sub-cloned into the MfeI-digested pGEM®-T-sU6 using Gibson Assembly© Master Mix (NEB, E2611S) to form final sgRNA expression vector pGEM®-T-sU6-sgRNA. A codon-optimized U6 promoter (sU6) (SEQ ID NO:7) was used to construct silkworm-specific gRNA (sgRNA) expression vectors. The hagfish silk genes (alpha and gamma) were designed and codon optimized for *Bombyx mori*, synthesized (Life Technologies), and concatenated to form two, three, and four repeats (alpha (2, 3, and 4) and gamma (2, 3, and 4)) using the enzymes AgeI and BspEI (NEB, R3552S and R0540S). To form the full FibH- and FibL-hagfish alpha and gamma vectors, the fragments of Alpha (3) and gamma (4) had been cut out from the original vectors by SalI and EcoRV (NEB, R3138S and R3195S). Then they were used to annealed with the PCR fragments (FibH-eGFP-DsRed-CTD and the FibL-NTD-eGFP-CTD) to form the full vectors of the FibH-eGFP-Alpha (3) or Gamma (4)-DsRed-CTD and the FibL-NTD-eGFP-Alpha (3) or Gamma (4)-CTD by Gibson assembly (NEB, E2611S). Designed PCR primers (Table 2) and the high fidelity master mix (NEB, M0541S) were used to get the fragments of the FibH-eGFP-DsRed-CTD and the FibL-NTD-eGFP-CTD from the previous spider silk constructs, the FibH-pSK-NTD-eGFP-MaSp1/MiSp1(8)-DsRed-CTD and the FibL-NTD-eGFP-MaSp1(6)-CTD.

TABLE 2

| Primers used for Gibson Assembly for HC- and LC- Alpha and Gamma Constructs | |
|---|---|
| Name | Sequence |
| HC-Alpha-F | SEQ ID NO: 15 |
| HC-Alpha-R | SEQ ID NO: 16 |
| HC-Gamma-F | SEQ ID NO: 17 |
| HC-Gamma-R | SEQ ID NO: 18 |
| LC-GA-alpha-F | SEQ ID NO: 19 |

TABLE 2-continued

Primers used for Gibson Assembly for HC-
and LC- Alpha and Gamma Constructs

| Name | Sequence |
|---|---|
| LC-GA-alpha-R | SEQ ID NO: 20 |
| LC-GA-Gamma-F | SEQ ID NO: 21 |
| LC-GA-Gamma-R | SEQ ID NO: 22 |

The hagfish thread keratin α amino acid sequence is SEQ ID NO: 8. The hagfish thread keratin γ amino acid sequence is SEQ ID NO: 9. The amino acid sequence for the *Bombyx mori* FibH is SEQ ID NO: 10. The amino acid sequence for the *Bombyx mori* FibL is SEQ ID NO: 11.

Transgenic Silkworm Isolation.

A silkworm strain with white cocoon was used for transformations, which facilitates the detection of the eGFP-tagged FibL-alpha/gamma proteins in FibL-transgenic cocoons. The FibH- and FibL-silkworm embryos were designed as zero generation ($G_0$) and their offspring were designed as the first and the second generations ($G_1$ and $G_2$). The green fluorescence of the FibH- or FibL-transgenic cocoons was detected under UV light in a dark room. The electroporation equipment, CUY21EDIT in vivo square wave electroporator and CUY495P10 chamber were purchased from Sonidel© Limited. Fresh eggs were collected within 1-2 h after being laid by purebred moths (Haoyue). The electroporation procedure is as follows: a) Prepare electroporation buffer (EP buffer) by adding ddH2O (385 µl), 2% PVP (polyvinylpyrrolidone) solution (250 µl), 10% Tween 20 (15 µl), 0.1 M spermidine solution (50 µl), DNA plasmid(s) solution (100 µg) specific for each transformed group to a 1.5 ml Eppendorf tube and mix; then add 100 µl 2.5 M $CaCl_2$, mixing well again; b) collect and briefly wash the silkworm eggs with purified water; c) place the eggs (500-1000 eggs) into the EP buffer in a 9 cm petri dish; d) treat the silkworm eggs with pressure reduction by placing the dish with eggs on ice in a vacuum chamber for 10-20 min; e) run electroporation for the eggs on ice by placing them into the electroporation chamber, adding 1 ml EP buffer into the electroporation chamber (eggs were cooled prior to electroporation by allowing them to sit in the chamber, on ice, for 2 min), and running the electroporation under 15 V, 50 ms (pulse), 75 ms (interval), 10-20 repeats, then leaving eggs in the chamber for 10-20 min on ice to allow the eggs to cool; f) place the eggs on ice and leave them for at least 1 h; g) eggs are then placed in a 9 cm petri dish with 7 cm diameter paper; and h) they are left in the dark at 25° C. for hatching.

Identification of the Transgenic Silkworms

After laying their eggs, the moths (heads, wings and abdomens) in each transgenic group (FibH-Alpha or Gamma; FibL-Alpha or Gamma) were subjected to genomic DNA extraction using the E.Z.N.A™ Insect DNA Isolation Kit (Omega Bio-Tek, C0926-01). The extracted genomic DNA was subjected to PCR for detection of the eGFP gene or stored at −20° C. The FibL or FibH-genome: junction testing had been performed by using the previous method 1. Briefly, the 3'- and 5'-end genome: transgene junction sequences were amplified using the designed primers. The first round of PCR amplification was performed with NEB-Next® High-Fidelity 2×PCR Master Mix (NEB, M0541S) and second round PCRs were performed using the PCR products purified from the first round of amplifications (Qiagen, Taq PCR Master Mix, No. 201443). Amplified fragments were gel-purified (Qiagen, No. 28704) and cloned into the pGEM®-T easy vector system (Promega, A3600) for sequencing. The sequencing data was analyzed using Blast at the National Center for Biotechnology Information (NCBI). The primers for eGFP detection and genome: junction testing please see Table 3.

Figure 3:
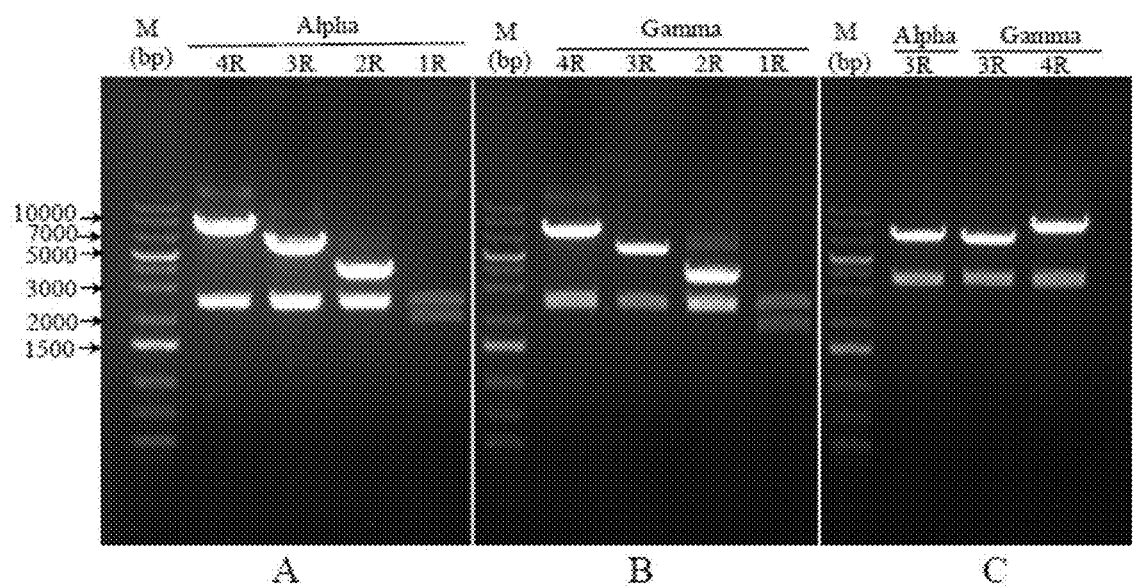
FIG. 3 shows gel images of the LC-Alpha and Gamma constructs.
Figure 4:
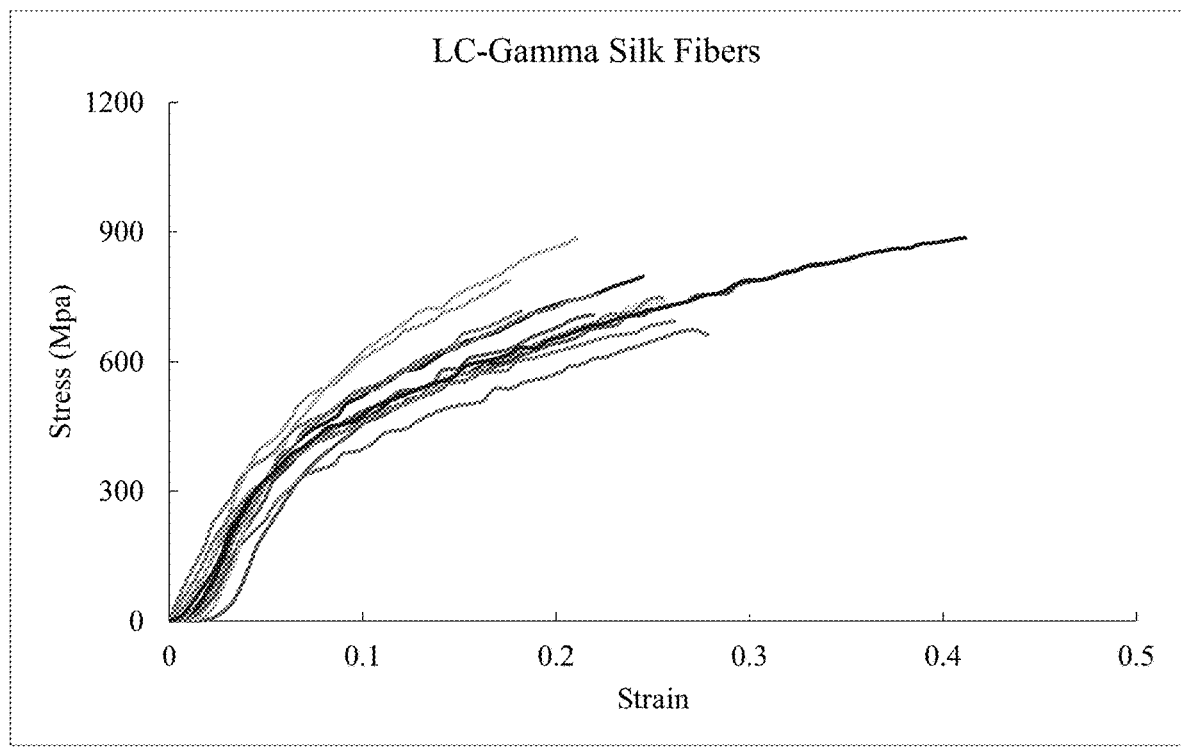
FIG. 4 shows the stress versus strain curve for hagfish thread keratin gamma fibers.
Figure 5:
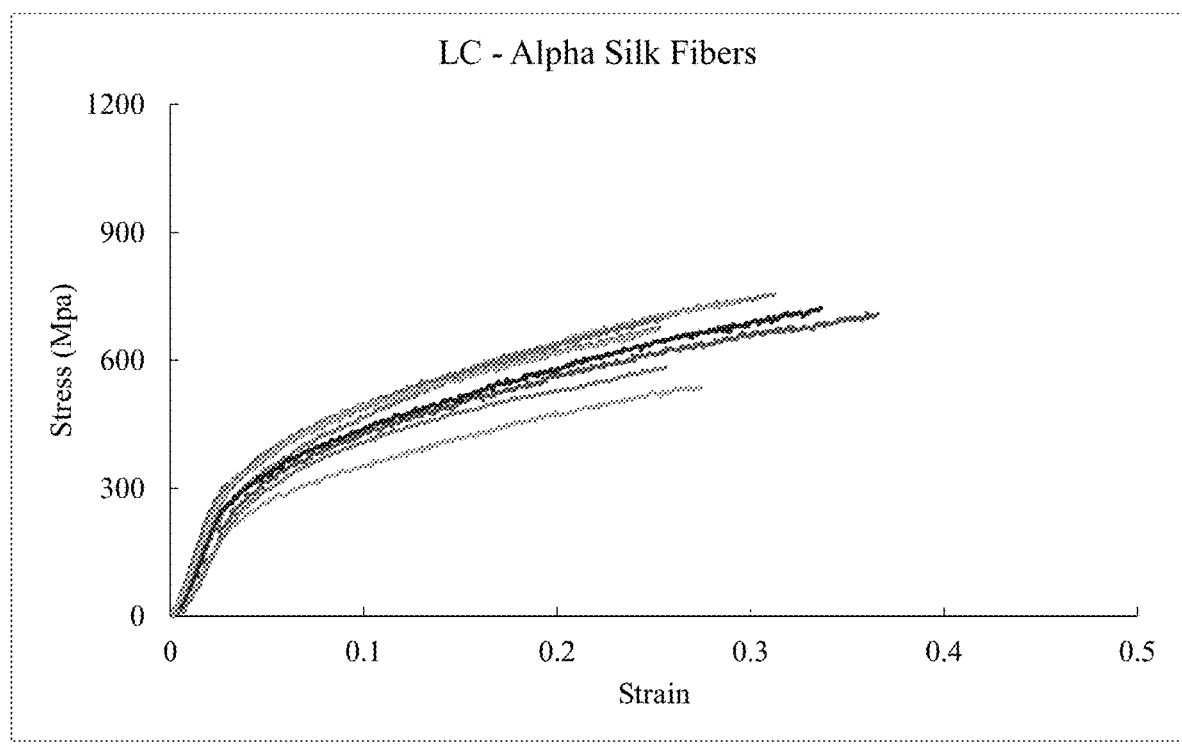
FIG. 5 shows the stress versus strain curve for hagfish thread keratin alpha fibers.
Figure 6:
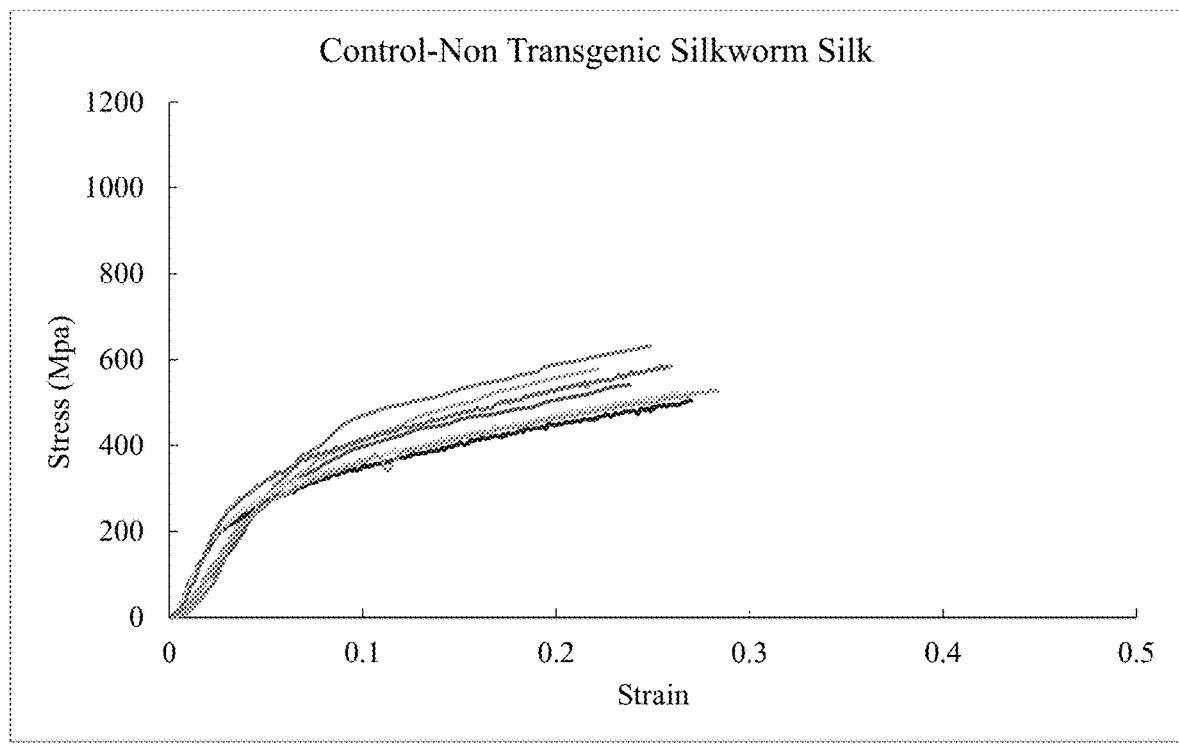
FIG. 6 shows the stress versus strain curve for silkworm fibers without hagfish thread keratin.
Figure 7:
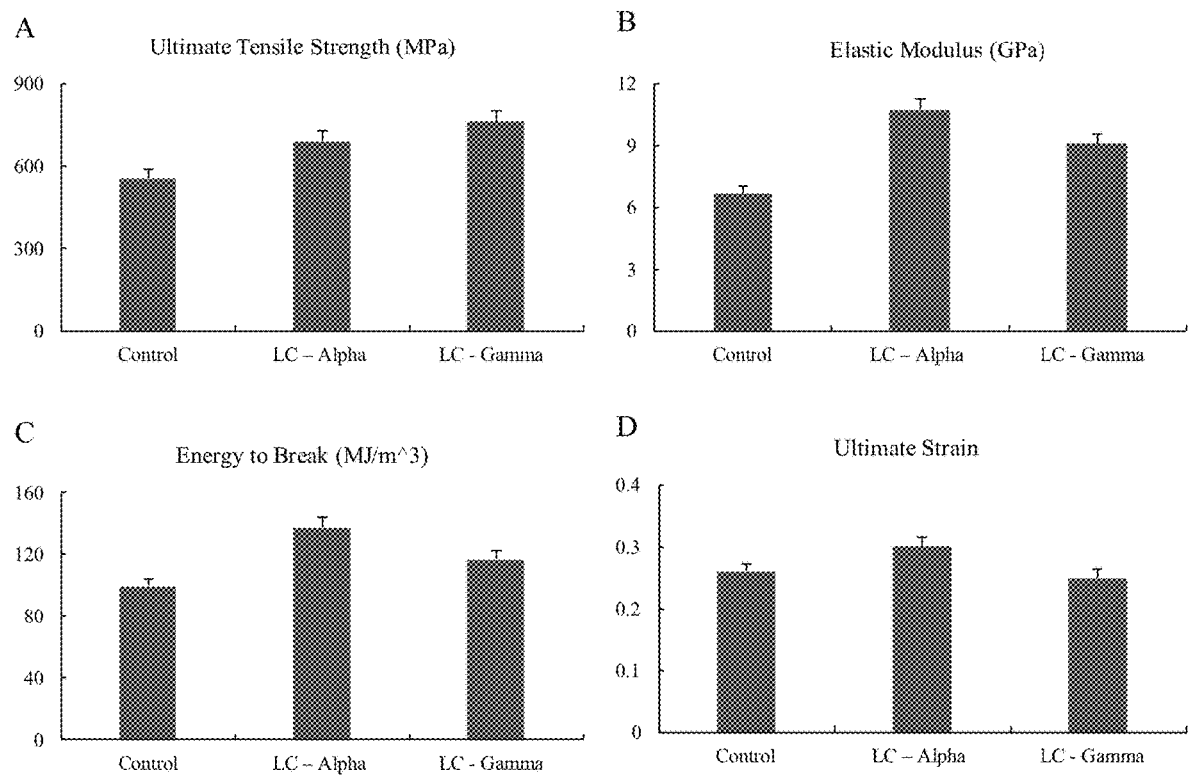
FIG. 7 shows mechanical properties of the hagfish thread keratin fiber compared to controls.

FIG. 3 shows western blot analysis used to identify transgenic silkworms transformed with alpha and gamma eGFP (Panel A) and NTD+ eGFP (Panel B). Detections indicated that the constructs of the alpha and/or gamma presented in the genome of the transgenic silkworms. NTD-GJ (Genome Junction) (Panel C) and CTD-GJ (Panel D) had shown that the constructs of the alpha and/or gamma integrated into the genome as designed.

TABLE 3

| Name | | Sequence | Primer Combinations for PCRs |
|---|---|---|---|
| eGFP | eGFP-SalI-F | SEQ ID NO: 23 | First - Forward |
| | eGFP-HindIII-R | SEQ ID NO: 24 | First - Reverse |
| DsRed | Dsred-BamHI | SEQ ID NO: 25 | First - Forward |
| | Dsred-XbaI | SEQ ID NO: 26 | First - Reverse |
| | HC_DsRed_1_F | SEQ ID NO: 27 | Secondary - Forward |
| | HC_DsRed_1_R | SEQ ID NO: 28 | Secondary - Reverse |
| | HC_DsRed_2_F | SEQ ID NO: 29 | Secondary - Forward |
| | HC_DsRed_2_R | SEQ ID NO: 30 | Secondary - Reverse |
| FibH | FibH62454-F | SEQ ID NO: 31 | 5' First - Forward |
| | H1-R | SEQ ID NO: 32 | 5' First - Reverse |
| | FibH62737-F | SEQ ID NO: 33 | 5' Secondary - Forward |
| | FibH-donor-R | SEQ ID NO: 34 | 5' Secondary - Reverse |
| | PSK-F | SEQ ID NO: 35 | 3' First - Forward |
| | FibH63746-R | SEQ ID NO: 36 | 3' First - Reverse |
| | PSK-F2 | SEQ ID NO: 37 | 3' Secondary - Forward |
| | FibH63575-R | SEQ ID NO: 38 | 3' Secondary - Reverse |
| FibL | LC-NHEJ-LJ13201-F | SEQ ID NO: 39 | 5' First - Forward |
| | LC-NHEJ-LJ13389-F | SEQ ID NO: 40 | 5' Secondary - Forward |
| | LJ-R1 | SEQ ID NO: 41 | 5' Secondary - Reverse |
| | LS-R | SEQ ID NO: 42 | 5' First - Reverse |
| | PSK-F | SEQ ID NO: 43 | 3' First - Forward |
| | PSK-F2 | SEQ ID NO: 44 | 3' Secondary - Forward |
| | LC-NHEJ-RJ14589-R | SEQ ID NO: 45 | 3' Secondary - Reverse |
| | Sac1-14600-R-R | SEQ ID NO: 46 | 3' First - Reverse |

Western Blot Analysis of the FibH- or FibL-Alpha/Gamma Proteins.

The FibH or FibL-transgenic silkworm glands (FibH- or FibL-Alpha/Gamma) were dissected from the FibH or FibL-transgenic silkworms at the third day of the fifth larval stage, washed with 1×PBS, and then stored at −80° C. The FibH or FibL-middle gland contents were homogenized in 2×SDS lysis buffer (3% SDS, 6 M urea, 40 mM Dithiothreitol, 10% w/v Glycerol, 0.01% Bromophenol blue, and 62.5 mM Tris-HCl pH 6.8), boiled at 100° C. for 15-20 min, and loaded onto 4-20% gradient gels (Thermo, Scientific), at 100 V for 1.5 h. After the SDS-PAGE, the FibH or FibL-middle gland proteins were transferred to Immobilon®-P Transfer Membrane (EMD Millipore, IPVH00010) using Tris-Glycine-Methanol buffer (25 mM Tris, 192 mM Glycine, and 10% methanol), at 45 V, overnight. The antibody staining process was performed as follows: 1) block the membrane for 1 h at room temperature (5% nonfat dry milk in 1×TBST as the blocking buffer); 2) incubate the membrane at 4° C. overnight with the diluted primary anti-eGFP antibody (1:1,000) (Thermo Scientific, MA1-952) or the diluted primary dsRed-2 antibody (1:500) (Santa Cruz® Biotechnology, sc-101529) in the blocking buffer; 3) wash the membrane three times with 1×TBST, 15 min each; 4) incubate the membrane with the diluted secondary antibody (1:1,000), Anti-Mouse IgG (H+L), alkaline phosphatase conjugated at room temperature for 1 h in the blocking buffer; 5) wash the membrane three times with 1×TBST, 15 min each; 6) the antibody-antigen reactions were performed using 1-Step™ NBT/BCIP substrate solution. The proteins of the non-transgenic silkworm glands were used as controls in all the experiments mentioned above. Each FibH or FibL-transgenic protein samples had three replicates as well as the control.

Figure 2:
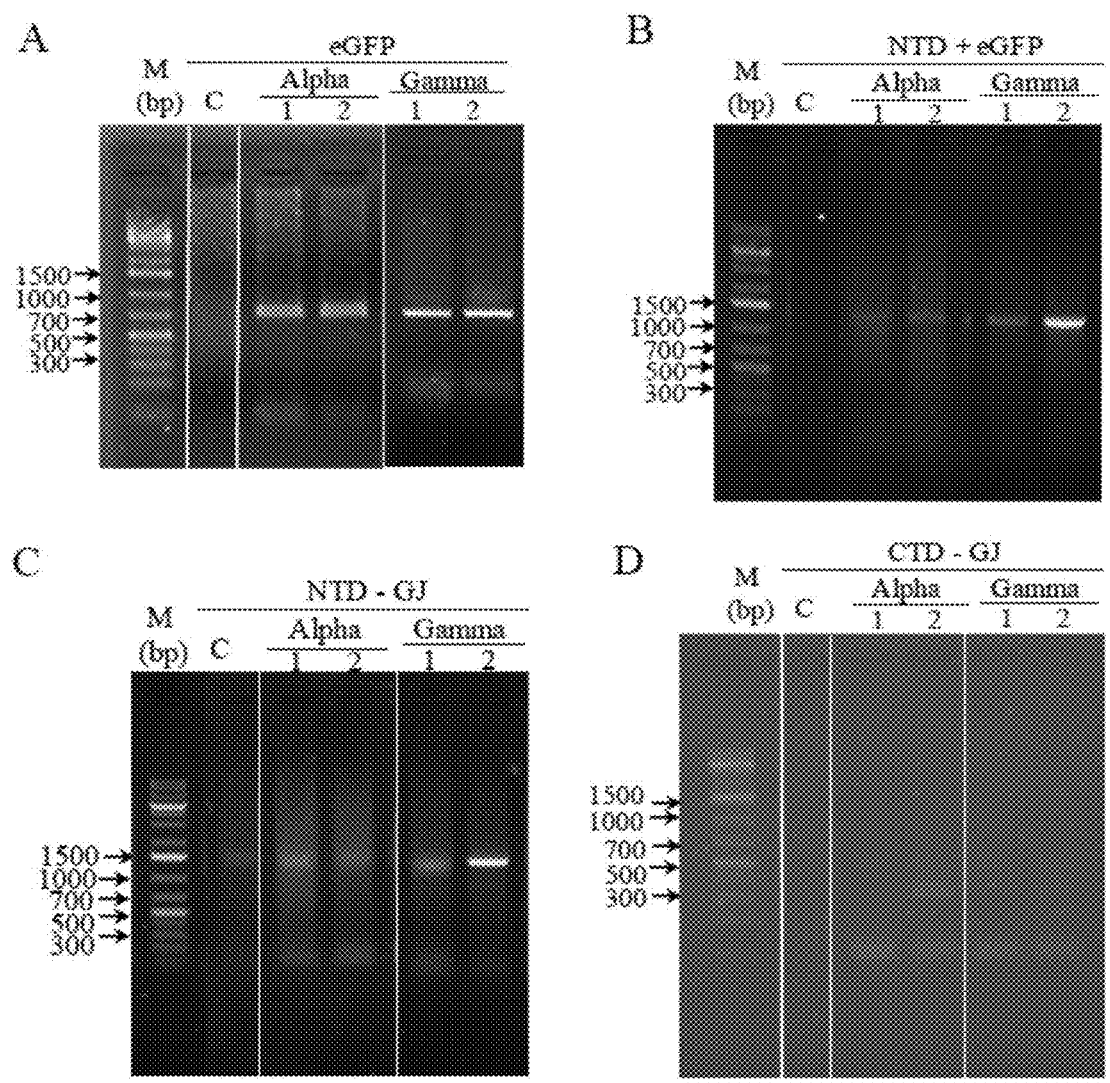
FIG. 2 shows gel images for identifying transgenic silkworms.

FIG. 3 shows the results from the western blot. In FIG. 2, Panel A: the four times (4R), three times (3R), two times (2R), and one time (1R) repeat of alpha gene in pMA-T vector, digested by SalI and EcoRV. Panel B: the four times (4R), three times (3R), two times (2R), and one time (1R) repeat of Gamma gene in pMA-T vector, digested by SalI and EcoRV. Panel C: the three times (3R) of alpha gene in the FibL-NTD-eGFP-CTD backbone vector; the three times (3R) and four times (4R) of gamma gene in the FibL-NTD-eGFP-CTD backbone vector; digested by KpnI and EcoRV.

Mechanical Properties of the Hagfish Thread Keratin Fibers.

The transgenic and control (non-transgenic) cocoon fibers were degummed (0.05% sodium bicarbonate, 0.05% SDS, and 0.01% sodium carbonate solution) at 85° C. for 30-45 min with a silk:solution ratio (weight/volume) of 1:50 until the silk became transparent. Then the degummed fibers were rinsed twice with warm water (50-60° C.) using the same material:solvent ratio. The degummed fibers were dried at room temperature overnight. Individual fibers from spiders and transgenic silkworms were gently separated to avoid stretching and deformation and then attached to "C" shaped cards using liquid super glue. Three individual fibers were taken from each cocoon in each group. The gauge length was 19.1 mm and diameters for each fiber were determined by taking an average of nine measurements with a Motic Optical 5A310 light microscope and Motic Images Plus 2.0 software. Each "C" card with the attached fiber was then loaded into a MTS Synergie 100 (MTS Systems) equipped with both a 50 N load cell and a custom 10 g load cell (Transducer Techniques) for mechanical testing. Using TestWorks® 4 software, the attached fiber was uniaxially tested by pulling the fiber at a speed of 50 mm/min with a data acquisition rate of 120 Hz until the fiber broke. All tests were performed in ambient conditions (20-22° C. and 20-26% humidity). Data were then exported and further analyzed using Microsoft Excel. Mean values and standard deviations (SD) were calculated from the raw data.

Table 4 below reports data showing the mechanical performance of the transgenic silkworm/hagfish thread keratin gamma fibers.

TABLE 4

| | Diameter (microns) | | Ultimate Tensile Strength (Ma) | | Energy to Break (MJ/m^3) | | Elastic Modulus (GPa) | | Ultimate Strain | |
|---|---|---|---|---|---|---|---|---|---|---|
| | Mean | Std | Mean | Std | Mean | Std | Mean | Std | Mean | Std |
| Control | 9.42 | 0.22 | 617.37 | 51.06 | 78.20 | 9.00 | 8.17 | 0.45 | 0.20 | 0.03 |
| Gamma4 | 8.23 | 0.5 | 759.33 | 62.04 | 116.84 | 25.92 | 9.06 | 1.07 | 0.25 | 0.05 |

The incorporation of the hagfish thread keratin gamma protein averagely made the transgenic fibers stronger and more flexible than the control fibers. Compared to the non-transgenic silkworm fibers, the average ultimate tensile strength of the transgenic hagfish-gamma/silkworm fibers was 759 MPa, increased 20% compared to the non-transgenic silkworm fibers. The average value of the energy to break was 117 MJ/m^3, a 50% increase in the transgenic hagfish-gamma/silkworm fibers. The average value of elastic modulus was 9 GPa, about a 11% increase in the transgenic hagfish-gamma/silkworm fibers. Additionally, the average value of the ultimate strain was increased 25% in the transgenic hagfish-gamma/silkworm fibers.

What is claimed is:

1. A transgenic silkworm whose genome comprises a nucleic acid encoding hagfish thread keratin, wherein the nucleic acid is stably integrated and is operably linked to an endogenous silkworm promoter, the transgenic silkworm produces a composite hagfish thread keratin silkworm silk protein in its silk gland and wherein the nucleic acid is selected from the group consisting of the sequence set forth in SEQ ID NO: 1, 2, 47 and 48.

2. The transgenic silkworm of claim 1, wherein the exogenous hagfish thread keratin gene is stably integrated in the intron of a fibroin heavy chain gene, FibH.

3. The transgenic silkworm of claim 2, wherein the exogenous hagfish thread keratin gene is stably integrated in a first intron of the fibroin heavy chain gene, FibH.

4. The transgenic silkworm of claim 1, wherein the exogenous hagfish thread keratin gene is stably integrated in an intron of a fibroin light chain gene, FibL.

5. The transgenic silkworm of claim 4, wherein the exogenous hagfish thread keratin gene is stably integrated in a sixth intron of the fibroin light chain gene, FibL.

6. The transgenic silkworm of claim 1, wherein the endogenous silkworm promoter is the silkworm-specific FibL promoter.

7. The transgenic silkworm of claim 1, wherein the exogenous hagfish thread keratin gene comprises a gene encoding *Eptatretus stoutii* thread keratin α or a gene encoding *Eptatretus stoutii* thread keratin γ.

8. The transgenic silkworm of claim 1, wherein the transgenic silkworm is *Bombyx* sp or *Bombyx mori*.

9. A progeny silkworm of the transgenic silkworm of claim 1, wherein the exogenous hagfish thread keratin gene is stably integrated.

10. A method for producing a transgenic silkworm, the method comprising:
introducing a nucleic acid encoding hagfish thread keratin into a defined site of the silkworm genome using a CRISPR/Cas9 system, wherein the nucleic acid is operably linked to an endogenous silkworm promoter, wherein the genome comprises the silkworm fibroin light chain (FibL) gene and heavy chain gene (FibH), wherein the nucleic acid is selected from the group consisting of the sequence set forth in SEQ ID NO: 1, 2, 47 and 48 and the transgenic silkworm produces a composite hagfish thread keratin silkworm silk protein in its silk gland.

* * * * *

SEQUENCE LISTING

<160> NUMBER OF SEQ ID NOS: 48

<210> SEQ ID NO 1
<211> LENGTH: 5790

```
<212> TYPE: DNA
<213> ORGANISM: Eptatretus stouti

<400> SEQUENCE: 1
agcatcagcc agaccgtgtc caaaagctac acaaaaagcg tgtcaagagg tggccaaggc      60
gtgtcatact cacaatcatc atcacacaaa gtcggaggtg gaagcgtcag atacggaaca     120
acatactcaa gcggaggaat cagcagagtg ctgggattcc aaggtggtgc tggtggtgca     180
gcttcagctg gattcggagg atcagtcggt ggatcaggac tgtcaagagt gctcggaggt     240
tcaatggtgt caggatacag atctggaatg ggtgtcggag gactgtctct gtctggaaca     300
gctggactgc ctgtgtcact gagaggtgtc ggtgctggaa aagctctgca cgctatcaca     360
agcgctttca gaacaagagt cggtggtcct ggaacatcag ttggaggata cggtgtcaac     420
tacagcttcc tgccttcaac agctggtcct tcattcggtg gacctttcgg aggaccattt     480
ggaggcccgt tcggaggtcc tctcggacct ggatatatcg accctgctac actgccttca     540
cctgacacag tgcaacacac cagaatccgc gaaaaacaag acctgcagac cctgaacacc     600
aagttcgcta acctggtgga ccaagtgcgc acactggaac aacacaacgc tatcctgaaa     660
gcccagatca gcatgatcac atcacctagc gacacacctg aaggacctgt gaacactgct     720
gtggtggctt caacagtgac agctacctac aacgctcaaa tcgaggacct gagaaccaca     780
aacactgctc tgcactcaga aatcgaccac ctgacaacca tcatcaacga catcaccacg     840
aagtacgagg aacaggtgga agtgacaaga acactggaaa ccgactggaa caccaacaag     900
gacaacatcg acaacaccta cctgacaatc gtggacctcc agacaaaagt gcaaggactg     960
gacgaacaga tcaacaccac caaacaaatc tacaacgcca gagtgcgcga agtgcaagct    1020
gctgtgacag gtggacctac agctgcttac tcaatcagag tggacaacac acaccaggct    1080
atcgacctga ctacaagcct gcaagaaatg aagacccact acgaagtgct ggctaccaaa    1140
agcagagaag aagctttcac acaggtccag cctcgcatcc aagaaatggc tgtgactgtg    1200
caggctggtc ctcaagctat catccaggct aaagaacaga tccacgtgtt caagctgcaa    1260
atcgacagcg tgcacagaga gattgacaga ctgcacagaa agaacaccga cgtggaacgc    1320
gaaatcaccg tgatcgaaac aaacatccac acgcagagcg acgagtggac taacaacatc    1380
aactcactga agtggacct ggaagtcatc aagaagcaga tcacacaata cgctcgcgac    1440
taccaagacc tcctggctac aaaaatgagc ctggacgtgg aaatcgctgc ctacaaaaaa    1500
ctgctggaca gcgaagaaac tcgcatctca cacggtggtg gaatcacaat cacaacaaac    1560
gctggaacat tcccaggtgg actgtcagct gctcctggtg gtggtgcttc atacgctatg    1620
gttccagctg gtgtcggcgg agttggattg gctggtgttg gtggttacgg attcagatca    1680
atgggaggtg gtgcggagt cggatatggt gctggcggag gtgcgttgg atatggcgtt    1740 ggtggtggat ttggaggtgg catgggaatg tcaatgagca gaatgtctat gggagctgct    1800
gtcggtggtg gttcttacgg atcaggatct ggatactctg gtggtttcgg actgtcatca    1860
tcaagagctg gatacagcgc tagcagaaag tcatactctt cagctagaag cagcagccgc    1920
atctacaccg gaagcatcag ccagaccgtg tccaaaagct acacaaaaag cgtgtcaaga    1980
ggtggccaag gcgtgtcata ctcacaatca tcatcacaca aagtcggagg tggaagcgtc    2040
agatacggaa caacatactc aagcggagga atcagcagag tgctgggatt ccaaggtggt    2100
gctggtggtg cagcttcagc tggattcgga ggatcagtcg gtggatcagg actgtcaaga    2160
gtgctcggag gttcaatggt gtcaggatac agatctggaa tgggtgtcgg aggactgtct    2220
```

```
ctgtctggaa cagctggact gcctgtgtca ctgagaggtg tcggtgctgg aaaagctctg    2280
cacgctatca caagcgcttt cagaacaaga gtcggtggtc ctggaacatc agttggagga    2340
tacggtgtca actacagctt cctgccttca acagctggtc cttcattcgg tggacctttc    2400
ggaggaccat ttggaggccc gttcggaggt cctctcggac ctggatatat cgaccctgct    2460
acactgcctt cacctgacac agtgcaacac accagaatcc gcgaaaaaca agacctgcag    2520
accctgaaca ccaagttcgc taacctggtg gaccaagtgc gcacactgga caacacaac    2580 gctatcctga agcccagat cagcatgatc acatcaccta gcgacacacc tgaaggacct    2640
gtgaacactg ctgtggtggc ttcaacagtg acagctacct acaacgctca atcgaggac    2700 ctgagaacca caaacactgc tctgcactca gaaatcgacc acctgacaac catcatcaac    2760
gacatcacca cgaagtacga ggaacaggtg gaagtgacaa gaacactgga aaccgactgg    2820
aacaccaaca aggacaacat cgacaacacc tacctgacaa tcgtggacct ccagacaaaa    2880
gtgcaaggac tggacgaaca gatcaacacc accaaacaaa tctacaacgc cagagtgcgc    2940
gaagtgcaag ctgctgtgac aggtggacct acagctgctt actcaatcag agtggacaac    3000
acacaccagg ctatcgacct gactacaagc ctgcaagaaa tgaagaccca ctacgaagtg    3060
ctggctacca aaagcagaga agaagctttc acacaggtcc agcctcgcat ccaagaaatg    3120
gctgtgactg tgcaggctgg tcctcaagct atcatccagg ctaaagaaca gatccacgtg    3180
ttcaagctgc aaatcgacag cgtgcacaga gagattgaca gactgcacag aaagaacacc    3240
gacgtggaac gcgaaatcac cgtgatcgaa acaaacatcc acacgcagag cgacgagtgg    3300
actaacaaca tcaactcact gaaagtggac ctggaagtca tcaagaagca gatcacacaa    3360
tacgctcgcg actaccaaga cctcctggct acaaaaatga gcctggacgt ggaaatcgct    3420
gcctacaaaa aactgctgga cagcgaagaa actcgcatct cacacggtgg tggaatcaca    3480
atcacaacaa cgctggaac attcccaggt ggactgtcag ctgctcctgg tggtggtgct    3540
tcatacgcta tggttccagc tggtgtcggc ggagttggat tggctggtgt tggtggttac    3600
ggattcagat caatgggagg tggtggcgga gtcggatatg gtgctggcgg aggtggcgtt    3660
ggatatggcg ttggtggtgg atttggaggt ggcatgggaa tgtcaatgag cagaatgtct    3720
atgggagctg ctgtcggtgg tggttcttac ggatcaggat ctggatactc tggtggtttc    3780
ggactgtcat catcaagagc tggatacagc gctagcagaa agtcatactc ttcagctaga    3840
agcagcagcc gcatctacac cggaagcatc agccagaccg tgtccaaaag ctacacaaaa    3900
agcgtgtcaa gaggtggcca aggcgtgtca tactcacaat catcatcaca caaagtcgga    3960
ggtggaagcg tcagatacgg aacaacatac tcaagcggag gaatcagcag agtgctggga    4020
ttccaaggtg gtgctggtgg tgcagcttca gctggattcg gaggatcagt cggtggatca    4080
ggactgtcaa gagtgctcgg aggttcaatg gtgtcaggat acagatctgg aatgggtgtc    4140
ggaggactgt ctctgtctgg aacagctgga ctgcctgtgt cactgagagg tgtcggtgct    4200
ggaaaagctc tgcacgctat cacaagcgct ttcagaacaa gagtcggtgg tcctggaaca    4260
tcagttggag gatacggtgt caactacagc ttcctgcctt caacagctgg tccttcattc    4320
ggtgaccttt cggaggacc atttggaggc ccgttcggag gtcctctcgg acctggatat    4380
atcgaccctg ctacactgcc ttcacctgac acagtgcaac acaccagaat ccgcgaaaaa    4440
caagacctgc agaccctgaa caccaagttc gctaacctgg tggaccaagt gcgcacactg    4500
gaacaacaca cgctatcct gaaagcccag atcagcatga tcacatcacc tagcgacaca    4560
cctgaaggac ctgtgaacac tgctgtggtg gcttcaacag tgacagctac ctacaacgct    4620
```

```
caaatcgagg acctgagaac cacaaacact gctctgcact cagaaatcga ccacctgaca    4680
accatcatca acgacatcac cacgaagtac gaggaacagg tggaagtgac aagaacactg    4740
gaaaccgact ggaacaccaa caaggacaac atcgacaaca cctacctgac aatcgtggac    4800
ctccagacaa aagtgcaagg actggacgaa cagatcaaca ccaccaaaca aatctacaac    4860
gccagagtgc gcgaagtgca agctgctgtg acaggtggac ctacagctgc ttactcaatc    4920
agagtggaca acacacacca ggctatcgac ctgactacaa gcctgcaaga aatgaagacc    4980
cactacgaag tgctggctac caaaagcaga gaagaagctt tcacacaggt ccagcctcgc    5040
atccaagaaa tggctgtgac tgtgcaggct ggtcctcaag ctatcatcca ggctaaagaa    5100
cagatccacg tgttcaagct gcaaatcgac agcgtgcaca gagagattga cagactgcac    5160
agaaagaaca ccgacgtgga acgcgaaatc accgtgatcg aaacaaacat ccacacgcag    5220
agcgacgagt ggactaacaa catcaactca ctgaaagtgg acctggaagt catcaagaag    5280
cagatcacac aatacgctcg cgactaccaa gacctcctgg ctacaaaaat gagcctggac    5340
gtggaaatcg ctgcctacaa aaaactgctg gacagcgaag aaactcgcat ctcacacggt    5400
ggtgaaatca caatcacaac aaacgctgga acattcccag gtggactgtc agctgctcct    5460
ggtggtggtg cttcatacgc tatggttcca gctggtgtcg gcggagttgg attggctggt    5520
gttggtggtt acggattcag atcaatggga ggtggtggcg gagtcggata tggtgctggc    5580
ggaggtggcg ttggatatgg cgttggtggt ggatttggag gtggcatggg aatgtcaatg    5640
agcagaatgt ctatgggagc tgctgtcggt ggtggttctt acggatcagg atctggatac    5700
tctggtggtt tcggactgtc atcatcaaga gctggataca gcgctagcag aaagtcatac    5760
tcttcagcta gaagcagcag ccgcatctac                                    5790
```

<210> SEQ ID NO 2
<211> LENGTH: 5430
<212> TYPE: DNA
<213> ORGANISM: Eptatretus stouti

<400> SEQUENCE: 2

```
gcttcacaca gcagcgtgtc atacagatca gtcagaacag gtggaaccag cgctatgatc     60
ggatcatcag gatacggtgg atcaagctca tcaagagcta tgggactcgg aatgggagct    120 gctgactgt caatgggtgg tggatcattc agagtgggat cagctggaat cggaggaatg    180
ggaatctcat ctggtattgg aggcatgggt atcagctcaa gagctggtgg aatgtctgct    240
tacggtggtg ctgctagcgg aggtgctggt ggattcgttt caggtggtgt ccctatgctc    300
ggatatggtg gtggcgctgg tggtttcatc ggtggtgtct cacctggaat catggcttca    360
ccagctttca cagctggtag agctatcaca tctgctggaa tgagcggagt cgtgggaaca    420
ttaggacctg ctggtggcat ggtgccttca ctggtgtcaa gagatgaagt gaaaaacatc    480
ctgggcaccc tgaaccagag actggcttca tacgtgaca aagtgcgcca gctgacaatc    540
gagaacgaaa ccatggaaga ggaactgaaa aacctgacag gcggagtgcc tatgtcacct    600
gactcaacag tgaacctgga aaacgtgaa acccaagtga ccgaaatgct gaccgaagtg    660
tctaacctga cactggaaag agtgcgcctg gaaatcgacg tggaccacct gagagctaca    720
gctgacgaaa tcaagtcgaa gtacgaattc gaactgggag tgcgcatgca gctggaaaca    780
gacattgcta acatgaagcg cgacctgaa gctgctaacg acatgagagt ggacctggac    840 agcaaaattca acttcctcac cgaagaactg accttccagc gcaaaacaca gatggaagaa    900
```

```
ctcaacaccc tgaaacagca gttcggtaga ctgggacctg tgcaaacatc agtgatcgag    960
ctggacaacg tgaaaagcgt gaacctgact gacgctctga acgtgatgcg cgaagaatac   1020
caacaggtgg tcaccaagaa cgtgcaagaa gctgaaacct actgcaagat gcagatcgac   1080
caaatccagg gaatcagcac acagacaacc gaacaaatca gcatcctgga caaagagatc   1140
aacacgctcg aaaaagaact gcagccgctg aacgtggaat accaaagact gctgacaacc   1200
taccagacac tgggagacag actgacagac ctgcagaaca gagaatcaat cgacctggtg   1260
cagttccaga acacatacac ccgctacgaa caagaaatcg aaggcaacca ggtggacctg   1320
caaagacaac tggtcacata ccaacaactg ctcgacgtga aaacagctct ggacgctgaa   1380
atcgccacct acaaaaaact gctggaaggc caagaactga tggtccgaac agctatggct   1440
gacgacttcg ctcacgctac agtcgtcaga tctggaacac tcggaggcgc ttcatcatca   1500
tcagtcggtt acggtgcttc aagcacaaca ctgggtgcta tctctggtgg atactctaca   1560
ggtggtggtg cttcatactc agctggtgct ggcggagctt cttattctgc tggtgccggt   1620
ggtgcctctt acggtgttgg tggtggttac tctggtggta gctcagctat gatggaagga   1680
tcatcatctg gtggccactc aatgtacagc tcgtctagca tgaagagaag cagcagcaaa   1740
tcagcttcag ctagcgctgg cggttacgga acatcaggac acgactcaac aatcatcctg   1800
cagcaaaccg gagcttcaca cagcagcgtg tcatacagat cagtcagaac aggtggaacc   1860
agcgctatga tcggatcatc aggatacggt ggatcaagct catcaagagc tatgggactc   1920
ggaatgggag ctgctggact gtcaatgggt ggtggatcat tcagagtggg atcagctgga   1980
atcggaggaa tgggaatctc atctggtatt ggaggcatgg gtatcagctc aagagctggt   2040
ggaatgtctg cttacggtgg tgctgctagc ggaggtgctg gtggattcgt ttcaggtggt   2100
gtccctatgc tcggatatgg tggtggcgct ggtggtttca tcggtggtgt ctcacctgga   2160
atcatggctt caccagcttt cacagctggt agagctatca catctgctgg aatgagcgga   2220
gtcgtgggaa cattaggacc tgctggtggc atggtgcctt cactggtgtc aagagatgaa   2280
gtgaaaaaca tcctgggcac cctgaaccag agactggctt catacgtgga caaagtgcgc   2340
cagctgacaa tcgagaacga aaccatggaa gaggaactga aaaacctgac aggcggagtg   2400
cctatgtcac ctgactcaac agtgaacctg gaaaacgtgg aaacccaagt gaccgaaatg   2460
ctgaccgaag tgtctaacct gacactggaa agagtgcgcc tggaaatcga cgtgaccac    2520 ctgagagcta cagctgacga aatcaagtcg aagtacgaat cgaactggg  agtgcgcatg   2580 cagctggaaa cagacattgc taacatgaag cgcgacctgg aagctgctaa cgacatgaga   2640
gtggacctgg acagcaaatt caacttcctc accgaagaac tgaccttcca gcgcaaaaca   2700
cagatgaaag aactcaacac cctgaaacag cagttcggta gactgggacc tgtgcaaaca   2760
tcagtgatcg agctggacaa cgtgaaaagc gtgaacctga ctgacgctct gaacgtgatg   2820
cgcgaagaat accaacaggt ggtcaccaag aacgtgcaag aagctgaaac ctactgcaag   2880
atgcagatcg accaaatcca gggaatcagc acacagacaa ccgaacaaat cagcatcctg   2940
gacaaagaga tcaacacgct cgaaaaagaa ctgcagccgc tgaacgtgga ataccaaaga   3000
ctgctgacaa cctaccagac actgggagac agactgacag acctgcagaa cagagaatca   3060
atcgacctgg tgcagttcca gaacacatac acccgctacg aacaagaaat cgaaggcaac   3120
caggtggacc tgcaaagaca actggtcaca taccaacaac tgctcgacgt gaaaacagct   3180
ctggacgctg aaatcgccac ctacaaaaaa ctgctggaag gccaagaact gatggtccga   3240
acagctatgg ctgacgactt cgctcacgct acagtcgtca gatctggaac actcggaggc   3300
```

```
gcttcatcat catcagtcgg ttacggtgct tcaagcacaa cactgggtgc tatctctggt    3360
ggatactcta caggtggtgg tgcttcatac tcagctggtg ctggcggagc ttcttattct    3420
gctggtgccg gtggtgcctc ttacggtgtt ggtggtggtt actctggtgg tagctcagct    3480
atgatggaag gatcatcatc tggtggccac tcaatgtaca gctcgtctag catgaagaga    3540
agcagcagca aatcagcttc agctagcgct ggcggttacg gaacatcagg acacgactca    3600
acaatcatcc tgcagcaaac cggagcttca cacagcagcg tgtcatacag atcagtcaga    3660
acaggtggaa ccagcgctat gatcggatca tcaggatacg gtggatcaag ctcatcaaga    3720
gctatgggac tcggaatggg agctgctgga ctgtcaatgg gtggtggatc attcagagtg    3780
ggatcagctg gaatcggagg aatgggaatc tcatctggta ttggaggcat gggtatcagc    3840
tcaagagctg gtggaatgtc tgcttacggt ggtgctgcta gcggaggtgc tggtggattc    3900
gtttcaggtg gtgtccctat gctcggatat ggtggtggcg ctggtggttt catcggtggt    3960
gtctcacctg gaatcatggc ttccaccagct ttcacagctg gtagagctat cacatctgct    4020
ggaatgagcg gagtcgtggg aacattagga cctgctggtg gcatggtgcc ttcactggtg    4080
tcaagagatg aagtgaaaaa catcctgggc accctgaacc agagactggc ttcatacgtg    4140
gacaaagtgc gccagctgac aatcgagaac gaaaccatgg aagaggaact gaaaaacctg    4200
acaggcggag tgcctatgtc acctgactca acagtgaacc tggaaaacgt ggaaacccaa    4260
gtgaccgaaa tgctgaccga agtgtctaac ctgacactgg aaagagtgcg cctggaaatc    4320
gacgtggacc acctgagagc tacagctgac gaaatcaagt cgaagtacga attcgaactg    4380
ggagtgcgca tgcagctgga aacagacatt gctaacatga gcgcgaccct ggaagctgct    4440
aacgacatga gagtggacct ggacagcaaa ttcaacttcc tcaccgaaga actgaccttc    4500
cagcgcaaaa cacagatgga agaactcaac accctgaaac agcagttcgg tagactggga    4560
cctgtgcaaa catcagtgat cgagctggac aacgtgaaaa gcgtgaacct gactgacgct    4620
ctgaacgtga tgcgcgaaga ataccaacag gtggtcacca agaacgtgca agaagctgaa    4680
acctactgca agatgcagat cgaccaaatc cagggaatca gcacacagac aaccgaacaa    4740
atcagcatcc tggacaaaga gatcaacacg ctcgaaaaag aactgcagcc gctgaacgtg    4800
gaataccaaa gactgctgac aacctaccag acactgggag acagactgac agacctgcag    4860
aacagagaat caatcgacct ggtgcagttc cagaacacat acacccgcta cgaacaagaa    4920
atcgaaggca accaggtgga cctgcaaaga caactggtca cataccaaca actgctcgac    4980
gtgaaaacag ctctggacgc tgaaatcgcc acctacaaaa aactgctgga aggccaagaa    5040
ctgatggtcc gaacagctat ggctgacgac ttcgctcacg ctacagtcgt cagatctgga    5100
acactcggag gcgcttcatc atcatcagtc ggttacggtg cttcaagcac aacactgggt    5160
gctatctctg gtggatactc tacaggtggt ggtgcttcat actcagctgg tgctggcgga    5220
gcttcttatt ctgctggtgc cggtggtgcc tcttacggtg ttggtggtgg ttactctggt    5280
ggtagctcag ctatgatgga aggatcatca tctggtggcc actcaatgta cagctcgtct    5340
agcatgaaga gaagcagcag caaatcagct tcagctagcg ctggcggtta cggaacatca    5400
ggacacgact caacaatcat cctgcagcaa                                     5430
```

<210> SEQ ID NO 3
<211> LENGTH: 20
<212> TYPE: DNA
<213> ORGANISM: Artificial Sequence
<220> FEATURE:

```
<223> OTHER INFORMATION: Primer 1 for gBlock DNA amplification

<400> SEQUENCE: 3
aggttatgta gtacacattg                                              20

<210> SEQ ID NO 4
<211> LENGTH: 19
<212> TYPE: DNA
<213> ORGANISM: Artificial Sequence
<220> FEATURE:
<223> OTHER INFORMATION: Primer 2 for gBlock DNA amplification

<400> SEQUENCE: 4
ttaatgccaa ctttgtaca                                               19

<210> SEQ ID NO 5
<211> LENGTH: 19
<212> TYPE: DNA
<213> ORGANISM: Artificial Sequence
<220> FEATURE:
<223> OTHER INFORMATION: Target site of gRNA HC-5

<400> SEQUENCE: 5
agaactttaa attatatct                                               19

<210> SEQ ID NO 6
<211> LENGTH: 19
<212> TYPE: DNA
<213> ORGANISM: Artificial Sequence
<220> FEATURE:
<223> OTHER INFORMATION: Target site of gRNA HC-6

<400> SEQUENCE: 6
tcactatgag acttaagct                                               19

<210> SEQ ID NO 7
<211> LENGTH: 604
<212> TYPE: DNA
<213> ORGANISM: Artificial Sequence
<220> FEATURE:
<223> OTHER INFORMATION: Codonoptimized U6 promoter (sU6)
<220> FEATURE:
<221> NAME/KEY: misc_feature
<222> LOCATION: (468)..(487)
<223> OTHER INFORMATION: n is a, c, g, t or u

<400> SEQUENCE: 7
aggttatgta gtacacattg ttgtaaatca ctgaattgtt ttagatgatt ttaacaatta    60
gtacttatta atattaaata agtacatacc ttgagaattt aaaaatcgtc aactataagc   120
catacgaatt taagcttggt acttggctta tagataagga cagaataaga attgttaacg   180
tgtaagacaa ggtcagatag tcatagtgat tttgtcaaag taataacaga tggcgctgta   240
caaaccataa ctgttttcat ttgttttat ggattttatt acaaattcta aaggttttat    300
tgttattatt taatttcgtt ttaattatat tatatatctt taatagaata tgttaagagt   360
ttttgctctt tttgaataat ctttgtaaag tcgagtgttg ttgtaaatca cgctttcaat   420
agtttagttt tttaggtat atatacaaaa tatcgtgctc tacaagtnnn nnnnnnnnn    480 nnnnnnngtt ttagagctag aaatagcaag ttaaaataag gctagtccgt tatcaacttg   540
aaaaagtggc accgagtcgg tgctttttt ctagacccag ctttcttgta caaagttggc    600
atta                                                              604
```

<210> SEQ ID NO 8
<211> LENGTH: 1927
<212> TYPE: PRT
<213> ORGANISM: Eptatretus stouti

<400> SEQUENCE: 8

```
Ser Ile Ser Gln Thr Val Ser Lys Ser Tyr Thr Lys Ser Val Ser Arg
1               5                   10                  15

Gly Gly Gln Gly Val Ser Tyr Ser Gln Ser Ser Ser His Lys Val Gly
            20                  25                  30

Gly Gly Ser Val Arg Tyr Gly Thr Tyr Ser Ser Gly Gly Ile Ser
        35                  40                  45

Arg Val Leu Gly Phe Gln Gly Gly Ala Gly Gly Ala Ser Ala Gly
    50                  55                  60

Phe Gly Gly Ser Val Gly Gly Ser Gly Leu Ser Arg Val Leu Gly Gly
65                  70                  75                  80

Ser Met Val Ser Gly Tyr Arg Ser Gly Met Gly Val Gly Gly Leu Ser
                85                  90                  95

Leu Ser Gly Thr Ala Gly Leu Pro Val Ser Leu Arg Gly Val Gly Ala
            100                 105                 110

Gly Lys Ala Leu His Ala Ile Thr Ser Ala Phe Arg Thr Arg Val Gly
        115                 120                 125

Gly Pro Gly Thr Ser Val Gly Gly Tyr Gly Val Asn Tyr Ser Phe Leu
    130                 135                 140

Pro Ser Thr Ala Gly Pro Ser Phe Gly Gly Pro Phe Gly Gly Pro Phe
145                 150                 155                 160

Gly Gly Pro Phe Gly Gly Pro Leu Gly Pro Gly Tyr Ile Asp Pro Ala
                165                 170                 175

Thr Leu Pro Ser Pro Asp Thr Val Gln His Thr Arg Ile Arg Glu Lys
            180                 185                 190

Gln Asp Leu Gln Thr Leu Asn Thr Lys Phe Ala Asn Leu Val Asp Gln
        195                 200                 205

Val Arg Thr Leu Glu Gln His Asn Ala Ile Leu Lys Ala Gln Ile Ser
    210                 215                 220

Met Ile Thr Ser Pro Ser Asp Thr Pro Glu Gly Pro Val Asn Thr Ala
225                 230                 235                 240

Val Val Ala Ser Thr Val Thr Ala Thr Tyr Asn Ala Gln Ile Glu Asp
                245                 250                 255

Leu Arg Thr Thr Asn Thr Ala Leu His Ser Glu Ile Asp His Leu Thr
            260                 265                 270

Thr Ile Ile Asn Asp Ile Thr Thr Lys Tyr Glu Glu Gln Val Glu Val
        275                 280                 285

Thr Arg Thr Leu Glu Thr Asp Trp Asn Thr Asn Lys Asp Asn Ile Asp
    290                 295                 300

Asn Thr Tyr Leu Thr Ile Val Asp Leu Gln Thr Lys Val Gln Gly Leu
305                 310                 315                 320

Asp Glu Gln Ile Asn Thr Thr Lys Gln Ile Tyr Asn Ala Arg Val Arg
                325                 330                 335

Glu Val Gln Ala Ala Val Thr Gly Gly Pro Thr Ala Thr Tyr Ser Ile
            340                 345                 350

Arg Val Asp Asn Thr His Gln Ala Ile Asp Leu Thr Thr Ser Leu Gln
        355                 360                 365

Glu Met Lys Thr His Tyr Glu Val Leu Ala Thr Lys Ser Arg Glu Glu
    370                 375                 380
```

```
Ala Phe Thr Gln Val Gln Pro Arg Ile Gln Glu Met Ala Val Thr Val
385                 390                 395                 400

Gln Ala Gly Pro Gln Ala Ile Ile Gln Ala Lys Glu Gln Ile His Val
            405                 410                 415

Phe Lys Leu Gln Ile Asp Ser Val His Arg Glu Ile Asp Arg Leu His
            420                 425                 430

Arg Lys Asn Thr Asp Val Glu Arg Glu Ile Thr Val Ile Glu Thr Asn
            435                 440                 445

Ile His Thr Gln Ser Asp Glu Trp Thr Asn Asn Ile Asn Ser Leu Lys
    450                 455                 460

Val Asp Leu Glu Val Ile Lys Lys Gln Ile Thr Gln Tyr Ala Arg Asp
465                 470                 475                 480

Tyr Gln Asp Leu Leu Ala Thr Lys Met Ser Leu Asp Val Glu Ile Ala
            485                 490                 495

Ala Tyr Lys Lys Leu Leu Asp Ser Glu Glu Thr Arg Ile Ser His Gly
            500                 505                 510

Gly Gly Ile Thr Ile Thr Thr Asn Ala Gly Thr Phe Pro Gly Gly Leu
            515                 520                 525

Ser Ala Ala Pro Gly Gly Gly Ala Ser Tyr Ala Met Val Pro Ala Gly
530                 535                 540

Val Gly Gly Val Gly Leu Ala Gly Val Gly Gly Tyr Gly Phe Arg Ser
545                 550                 555                 560

Met Gly Gly Gly Gly Val Gly Tyr Gly Ala Gly Gly Gly Val
            565                 570                 575

Gly Tyr Gly Val Gly Gly Phe Gly Gly Met Gly Met Ser Met
            580                 585                 590

Ser Arg Met Ser Met Gly Ala Ala Gly Gly Ser Tyr Gly Ser Gly
            595                 600                 605

Ser Gly Tyr Ser Gly Gly Phe Gly Leu Ser Ser Arg Ala Gly Tyr
    610                 615                 620

Ser Ala Ser Arg Lys Ser Tyr Ser Ser Ala Arg Ser Ser Ser Arg Ile
625                 630                 635                 640

Tyr Thr Gly Ser Ile Ser Gln Thr Val Ser Lys Ser Tyr Thr Lys Ser
            645                 650                 655

Val Ser Arg Gly Gly Gln Gly Val Ser Tyr Ser Gln Ser Ser Ser His
            660                 665                 670

Lys Val Gly Gly Gly Ser Val Arg Tyr Gly Thr Thr Tyr Ser Ser Gly
            675                 680                 685

Gly Ile Ser Arg Val Leu Gly Phe Gln Gly Gly Ala Gly Gly Ala
    690                 695                 700

Ser Ala Gly Phe Gly Gly Ser Val Gly Gly Ser Gly Leu Ser Arg Val
705                 710                 715                 720

Leu Gly Gly Ser Met Val Ser Gly Tyr Arg Ser Gly Met Gly Val Gly
            725                 730                 735

Gly Leu Ser Leu Ser Gly Thr Ala Gly Leu Pro Val Ser Leu Arg Gly
            740                 745                 750

Val Gly Ala Gly Lys Ala Leu His Ala Ile Thr Ser Ala Phe Arg Thr
            755                 760                 765

Arg Val Gly Gly Pro Gly Thr Ser Val Gly Gly Tyr Gly Val Asn Tyr
            770                 775                 780

Ser Phe Leu Pro Ser Thr Ala Gly Pro Ser Phe Gly Gly Pro Phe Gly
785                 790                 795                 800

Gly Pro Phe Gly Gly Pro Phe Gly Gly Pro Leu Gly Pro Gly Tyr Ile
```

-continued

```
                805                 810                 815
Asp Pro Ala Thr Leu Pro Ser Pro Asp Thr Val Gln His Thr Arg Ile
            820                 825                 830

Arg Glu Lys Gln Asp Leu Gln Thr Leu Asn Thr Lys Phe Ala Asn Leu
            835                 840                 845

Val Asp Gln Val Arg Thr Leu Glu Gln His Asn Ala Ile Leu Lys Ala
850                 855                 860

Gln Ile Ser Met Ile Thr Ser Pro Ser Asp Thr Pro Glu Gly Pro Val
865                 870                 875                 880

Asn Thr Ala Val Val Ala Ser Thr Val Thr Ala Thr Tyr Asn Ala Gln
            885                 890                 895

Ile Glu Asp Leu Arg Thr Thr Asn Thr Ala Leu His Ser Glu Ile Asp
            900                 905                 910

His Leu Thr Thr Ile Ile Asn Asp Ile Thr Thr Lys Tyr Glu Glu Gln
            915                 920                 925

Val Glu Val Thr Arg Thr Leu Glu Thr Asp Trp Asn Thr Asn Lys Asp
            930                 935                 940

Asn Ile Asp Asn Thr Tyr Leu Thr Ile Val Asp Leu Gln Thr Lys Val
945                 950                 955                 960

Gln Gly Leu Asp Glu Gln Ile Asn Thr Thr Lys Gln Ile Tyr Asn Ala
            965                 970                 975

Arg Val Arg Glu Val Gln Ala Ala Val Thr Gly Gly Pro Thr Ala Ala
            980                 985                 990

Tyr Ser Ile Arg Val Asp Asn Thr His Gln Ala Ile Asp Leu Thr Thr
            995                 1000                1005

Ser Leu Gln Glu Met Lys Thr His Tyr Glu Val Leu Ala Thr Lys
    1010                1015                1020

Ser Arg Glu Glu Ala Phe Thr Gln Val Gln Pro Arg Ile Gln Glu
    1025                1030                1035

Met Ala Val Thr Val Gln Ala Gly Pro Gln Ala Ile Ile Gln Ala
    1040                1045                1050

Lys Glu Gln Ile His Val Phe Lys Leu Gln Ile Asp Ser Val His
    1055                1060                1065

Arg Glu Ile Asp Arg Leu His Arg Lys Asn Thr Asp Val Glu Arg
    1070                1075                1080

Glu Ile Thr Val Ile Glu Thr Asn Ile His Thr Gln Ser Asp Glu
    1085                1090                1095

Trp Thr Asn Asn Ile Asn Ser Leu Lys Val Asp Leu Glu Val Ile
    1100                1105                1110

Lys Lys Gln Ile Thr Gln Tyr Ala Arg Asp Tyr Gln Asp Leu Leu
    1115                1120                1125

Ala Thr Lys Met Ser Leu Asp Val Glu Ile Ala Ala Tyr Lys Lys
    1130                1135                1140

Leu Leu Asp Ser Glu Glu Thr Arg Ile Ser His Gly Gly Gly Ile
    1145                1150                1155

Thr Ile Thr Thr Asn Ala Gly Thr Phe Pro Gly Gly Leu Ser Ala
    1160                1165                1170

Ala Pro Gly Gly Gly Ala Ser Tyr Ala Met Val Pro Ala Gly Val
    1175                1180                1185

Gly Gly Val Gly Leu Ala Gly Val Gly Gly Tyr Gly Phe Arg Ser
    1190                1195                1200

Met Gly Gly Gly Gly Val Gly Tyr Gly Ala Gly Gly Gly Gly
    1205                1210                1215
```

-continued

```
Val Gly Tyr Gly Val Gly Gly Phe Gly Gly Met Gly Met
1220            1225            1230

Ser Met Ser Arg Met Ser Met Gly Ala Ala Gly Gly Ser Tyr
1235            1240            1245

Gly Ser Gly Ser Gly Tyr Ser Gly Gly Phe Gly Leu Ser Ser Ser
1250            1255            1260

Arg Ala Gly Tyr Ser Ala Ser Arg Lys Ser Tyr Ser Ser Ala Arg
1265            1270            1275

Ser Ser Ser Arg Ile Tyr Thr Gly Ser Ile Ser Gln Thr Val Ser
1280            1285            1290

Lys Ser Tyr Thr Lys Ser Val Ser Arg Gly Gly Gln Gly Val Ser
1295            1300            1305

Tyr Ser Gln Ser Ser Ser His Lys Val Gly Gly Ser Val Arg
1310            1315            1320

Tyr Gly Thr Thr Tyr Ser Ser Gly Gly Ile Ser Arg Val Leu Gly
1325            1330            1335

Phe Gln Gly Gly Ala Gly Gly Ala Ala Ser Ala Gly Phe Gly Gly
1340            1345            1350

Ser Val Gly Gly Ser Gly Leu Ser Arg Val Leu Gly Gly Ser Met
1355            1360            1365

Val Ser Gly Tyr Arg Ser Gly Met Gly Val Gly Gly Leu Ser Leu
1370            1375            1380

Ser Gly Thr Ala Gly Leu Pro Val Ser Leu Arg Gly Val Gly Ala
1385            1390            1395

Gly Lys Ala Leu His Ala Ile Thr Ser Ala Phe Arg Thr Arg Val
1400            1405            1410

Gly Gly Pro Gly Thr Ser Val Gly Gly Tyr Gly Val Asn Tyr Ser
1415            1420            1425

Phe Leu Pro Ser Thr Ala Gly Pro Ser Phe Gly Gly Pro Phe Gly
1430            1435            1440

Gly Pro Phe Gly Gly Pro Phe Gly Gly Pro Leu Gly Pro Gly Tyr
1445            1450            1455

Ile Asp Pro Ala Thr Leu Pro Ser Pro Asp Thr Val Gln His Thr
1460            1465            1470

Arg Ile Arg Glu Lys Gln Asp Leu Gln Thr Leu Asn Thr Lys Phe
1475            1480            1485

Ala Asn Leu Val Asp Gln Val Arg Thr Leu Glu Gln His Asn Ala
1490            1495            1500

Ile Leu Lys Ala Gln Ile Ser Met Ile Thr Ser Pro Ser Asp Thr
1505            1510            1515

Pro Glu Gly Pro Val Asn Thr Ala Val Val Ala Ser Thr Val Thr
1520            1525            1530

Ala Thr Tyr Asn Ala Gln Ile Glu Asp Leu Arg Thr Thr Asn Thr
1535            1540            1545

Ala Leu His Ser Glu Ile Asp His Leu Thr Thr Ile Ile Asn Asp
1550            1555            1560

Ile Thr Thr Lys Tyr Glu Glu Gln Val Glu Val Thr Arg Thr Leu
1565            1570            1575

Glu Thr Asp Trp Asn Thr Asn Lys Asp Asn Ile Asp Asn Thr Tyr
1580            1585            1590

Leu Thr Ile Val Asp Leu Gln Thr Lys Val Gln Gly Leu Asp Glu
1595            1600            1605
```

```
Gln Ile Asn Thr Thr Lys Gln Ile Tyr Asn Ala Arg Val Arg Glu
    1610                1615                1620

Val Gln Ala Ala Val Thr Gly Gly Pro Thr Ala Ala Tyr Ser Ile
    1625                1630                1635

Arg Val Asp Asn Thr His Gln Ala Ile Asp Leu Thr Thr Ser Leu
    1640                1645                1650

Gln Glu Met Lys Thr His Tyr Glu Val Leu Ala Thr Lys Ser Arg
    1655                1660                1665

Glu Glu Ala Phe Thr Gln Val Gln Pro Arg Ile Gln Glu Met Ala
    1670                1675                1680

Val Thr Val Gln Ala Gly Pro Gln Ala Ile Ile Gln Ala Lys Glu
    1685                1690                1695

Gln Ile His Val Phe Lys Leu Gln Ile Asp Ser Val His Arg Glu
    1700                1705                1710

Ile Asp Arg Leu His Arg Lys Asn Thr Asp Val Glu Arg Glu Ile
    1715                1720                1725

Thr Val Ile Glu Thr Asn Ile His Thr Gln Ser Asp Glu Trp Thr
    1730                1735                1740

Asn Asn Ile Asn Ser Leu Lys Val Asp Leu Glu Val Ile Lys Lys
    1745                1750                1755

Gln Ile Thr Gln Tyr Ala Arg Asp Tyr Gln Asp Leu Leu Ala Thr
    1760                1765                1770

Lys Met Ser Leu Asp Val Glu Ile Ala Ala Tyr Lys Lys Leu Leu
    1775                1780                1785

Asp Ser Glu Glu Thr Arg Ile Ser His Gly Gly Gly Ile Thr Ile
    1790                1795                1800

Thr Thr Asn Ala Gly Thr Phe Pro Gly Gly Leu Ser Ala Ala Pro
    1805                1810                1815

Gly Gly Gly Ala Ser Tyr Ala Met Val Pro Ala Gly Val Gly Gly
    1820                1825                1830

Val Gly Leu Ala Gly Val Gly Gly Tyr Gly Phe Arg Ser Met Gly
    1835                1840                1845

Gly Gly Gly Gly Val Gly Tyr Gly Ala Gly Gly Gly Gly Val Gly
    1850                1855                1860

Tyr Gly Val Gly Gly Gly Phe Gly Gly Gly Met Gly Met Ser Met
    1865                1870                1875

Ser Arg Met Ser Met Gly Ala Ala Gly Gly Ser Tyr Gly Ser
    1880                1885                1890

Gly Ser Gly Tyr Ser Gly Gly Phe Gly Leu Ser Ser Ser Arg Ala
    1895                1900                1905

Gly Tyr Ser Ala Ser Arg Lys Ser Tyr Ser Ser Ala Arg Ser Ser
    1910                1915                1920

Ser Arg Ile Tyr
    1925

<210> SEQ ID NO 9
<211> LENGTH: 1810
<212> TYPE: PRT
<213> ORGANISM: Eptatretus stouti

<400> SEQUENCE: 9

Ala Ser His Ser Ser Val Ser Tyr Arg Ser Val Arg Thr Gly Gly Thr
1               5                   10                  15

Ser Ala Met Ile Gly Ser Ser Gly Tyr Gly Gly Ser Ser Ser Ser Arg
            20                  25                  30
```

-continued

```
Ala Met Gly Leu Gly Met Gly Ala Ala Gly Leu Ser Met Gly Gly
         35                  40                  45
Ser Phe Arg Val Gly Ser Ala Gly Ile Gly Gly Met Gly Ile Ser Ser
    50                  55                  60
Gly Ile Gly Gly Met Gly Ile Ser Ser Arg Ala Gly Gly Met Ser Ala
65                  70                  75                  80
Tyr Gly Gly Ala Ala Ser Gly Gly Ala Gly Gly Phe Val Ser Gly Gly
                85                  90                  95
Val Pro Met Leu Gly Tyr Gly Gly Ala Gly Gly Phe Ile Gly Gly
            100                 105                 110
Val Ser Pro Gly Ile Met Ala Ser Pro Ala Phe Thr Ala Gly Arg Ala
        115                 120                 125
Ile Thr Ser Ala Gly Met Ser Gly Val Val Gly Thr Leu Gly Pro Ala
    130                 135                 140
Gly Gly Met Val Pro Ser Leu Val Ser Arg Asp Glu Val Lys Asn Ile
145                 150                 155                 160
Leu Gly Thr Leu Asn Gln Arg Leu Ala Ser Tyr Val Asp Lys Val Arg
                165                 170                 175
Gln Leu Thr Ile Glu Asn Glu Thr Met Glu Glu Leu Lys Asn Leu
            180                 185                 190
Thr Gly Gly Val Pro Met Ser Pro Asp Ser Thr Val Asn Leu Glu Asn
        195                 200                 205
Val Glu Thr Gln Val Thr Glu Met Leu Thr Glu Val Ser Asn Leu Thr
    210                 215                 220
Leu Glu Arg Val Arg Leu Glu Ile Asp Val Asp His Leu Arg Ala Thr
225                 230                 235                 240
Ala Asp Glu Ile Lys Ser Lys Tyr Glu Phe Glu Leu Gly Val Arg Met
                245                 250                 255
Gln Leu Glu Thr Asp Ile Ala Asn Met Lys Arg Asp Leu Glu Ala Ala
            260                 265                 270
Asn Asp Met Arg Val Asp Leu Asp Ser Lys Phe Asn Phe Leu Thr Glu
        275                 280                 285
Glu Leu Thr Phe Gln Arg Lys Thr Gln Met Glu Glu Leu Asn Thr Leu
    290                 295                 300
Lys Gln Gln Phe Gly Arg Leu Gly Pro Val Gln Thr Ser Val Ile Glu
305                 310                 315                 320
Leu Asp Asn Val Lys Ser Val Asn Leu Thr Asp Ala Leu Asn Val Met
                325                 330                 335
Arg Glu Glu Tyr Gln Gln Val Val Thr Lys Asn Val Gln Glu Ala Glu
            340                 345                 350
Thr Tyr Cys Lys Met Gln Ile Asp Gln Ile Gln Gly Ile Ser Thr Gln
        355                 360                 365
Thr Thr Glu Gln Ile Ser Ile Leu Asp Lys Glu Ile Asn Thr Leu Glu
    370                 375                 380
Lys Glu Leu Gln Pro Leu Asn Val Glu Tyr Gln Arg Leu Leu Thr Thr
385                 390                 395                 400
Tyr Gln Thr Leu Gly Asp Arg Leu Thr Asp Leu Gln Asn Arg Glu Ser
                405                 410                 415
Ile Asp Leu Val Gln Phe Gln Asn Thr Tyr Thr Arg Tyr Glu Gln Glu
            420                 425                 430
Ile Glu Gly Asn Gln Val Asp Leu Gln Arg Gln Leu Val Thr Tyr Gln
        435                 440                 445
```

-continued

Gln Leu Leu Asp Val Lys Thr Ala Leu Asp Ala Glu Ile Ala Thr Tyr
    450                 455                 460

Lys Lys Leu Leu Glu Gly Gln Glu Leu Met Val Arg Thr Ala Met Ala
465                 470                 475                 480

Asp Asp Phe Ala His Ala Thr Val Val Arg Ser Gly Thr Leu Gly Gly
            485                 490                 495

Ala Ser Ser Ser Val Gly Tyr Gly Ala Ser Ser Thr Thr Leu Gly
        500                 505                 510

Ala Ile Ser Gly Gly Tyr Ser Thr Gly Gly Ala Ser Tyr Ser Ala
        515                 520                 525

Gly Ala Gly Gly Ala Ser Tyr Ser Ala Gly Ala Gly Ala Ser Tyr
530                 535                 540

Gly Val Gly Gly Tyr Ser Gly Gly Ser Ser Ala Met Met Glu Gly
545                 550                 555                 560

Ser Ser Ser Gly Gly His Ser Met Tyr Ser Ser Ser Met Lys Arg
                565                 570                 575

Ser Ser Ser Lys Ser Ala Ser Ala Ser Ala Gly Gly Tyr Gly Thr Ser
            580                 585                 590

Gly His Asp Ser Thr Ile Ile Leu Gln Gln Thr Gly Ala Ser His Ser
        595                 600                 605

Ser Val Ser Tyr Arg Ser Val Arg Thr Gly Gly Thr Ser Ala Met Ile
    610                 615                 620

Gly Ser Ser Gly Tyr Gly Gly Ser Ser Ser Arg Ala Met Gly Leu
625                 630                 635                 640

Gly Met Gly Ala Ala Gly Leu Ser Met Gly Gly Gly Ser Phe Arg Val
            645                 650                 655

Gly Ser Ala Gly Ile Gly Gly Met Gly Ile Ser Ser Gly Ile Gly Gly
        660                 665                 670

Met Gly Ile Ser Ser Arg Ala Gly Gly Met Ser Ala Tyr Gly Gly Ala
        675                 680                 685

Ala Ser Gly Gly Ala Gly Gly Phe Val Ser Gly Gly Val Pro Met Leu
    690                 695                 700

Gly Tyr Gly Gly Gly Ala Gly Gly Phe Ile Gly Gly Val Ser Pro Gly
705                 710                 715                 720

Ile Met Ala Ser Pro Ala Phe Thr Ala Gly Arg Ala Ile Thr Ser Ala
            725                 730                 735

Gly Met Ser Gly Val Val Gly Thr Leu Gly Pro Ala Gly Gly Met Val
        740                 745                 750

Pro Ser Leu Val Ser Arg Asp Glu Val Lys Asn Ile Leu Gly Thr Leu
    755                 760                 765

Asn Gln Arg Leu Ala Ser Tyr Val Asp Lys Val Arg Gln Leu Thr Ile
770                 775                 780

Glu Asn Glu Thr Met Glu Glu Leu Lys Asn Leu Thr Gly Gly Val
785                 790                 795                 800

Pro Met Ser Pro Asp Ser Thr Val Asn Leu Glu Asn Val Glu Thr Gln
            805                 810                 815

Val Thr Glu Met Leu Thr Glu Val Ser Asn Leu Thr Leu Glu Arg Val
        820                 825                 830

Arg Leu Glu Ile Asp Val Asp His Leu Arg Ala Thr Ala Asp Glu Ile
        835                 840                 845

Lys Ser Lys Tyr Glu Phe Glu Leu Gly Val Arg Met Gln Leu Glu Thr
    850                 855                 860

Asp Ile Ala Asn Met Lys Arg Asp Leu Glu Ala Ala Asn Asp Met Arg

```
865                 870                 875                 880
Val Asp Leu Asp Ser Lys Phe Asn Phe Leu Thr Glu Glu Leu Thr Phe
                885                 890                 895
Gln Arg Lys Thr Gln Met Glu Glu Leu Asn Thr Leu Lys Gln Gln Phe
                900                 905                 910
Gly Arg Leu Gly Pro Val Gln Thr Ser Val Ile Glu Leu Asp Asn Val
                915                 920                 925
Lys Ser Val Asn Leu Thr Asp Ala Leu Asn Val Met Arg Glu Glu Tyr
                930                 935                 940
Gln Gln Val Val Thr Lys Asn Val Gln Glu Ala Glu Thr Tyr Cys Lys
945                 950                 955                 960
Met Gln Ile Asp Gln Ile Gln Gly Ile Ser Thr Gln Thr Thr Glu Gln
                965                 970                 975
Ile Ser Ile Leu Asp Lys Glu Ile Asn Thr Leu Glu Lys Glu Leu Gln
                980                 985                 990
Pro Leu Asn Val Glu Tyr Gln Arg Leu Leu Thr Thr Tyr Gln Thr Leu
                995                 1000                1005
Gly Asp Arg Leu Thr Asp Leu Gln Asn Arg Glu Ser Ile Asp Leu
        1010                1015                1020
Val Gln Phe Gln Asn Thr Tyr Thr Arg Tyr Glu Gln Glu Ile Glu
        1025                1030                1035
Gly Asn Gln Val Asp Leu Gln Arg Gln Leu Val Thr Tyr Gln Gln
        1040                1045                1050
Leu Leu Asp Val Lys Thr Ala Leu Asp Ala Glu Ile Ala Thr Tyr
        1055                1060                1065
Lys Lys Leu Leu Glu Gly Gln Glu Leu Met Val Arg Thr Ala Met
        1070                1075                1080
Ala Asp Asp Phe Ala His Ala Thr Val Val Arg Ser Gly Thr Leu
        1085                1090                1095
Gly Gly Ala Ser Ser Ser Val Gly Tyr Gly Ala Ser Ser Thr
        1100                1105                1110
Thr Leu Gly Ala Ile Ser Gly Gly Tyr Ser Thr Gly Gly Gly Ala
        1115                1120                1125
Ser Tyr Ser Ala Gly Ala Gly Gly Ala Ser Tyr Ser Ala Gly Ala
        1130                1135                1140
Gly Gly Ala Ser Tyr Gly Val Gly Gly Gly Tyr Ser Gly Gly Ser
        1145                1150                1155
Ser Ala Met Met Glu Gly Ser Ser Gly Gly His Ser Met Tyr
        1160                1165                1170
Ser Ser Ser Ser Met Lys Arg Ser Ser Ser Lys Ser Ala Ser Ala
        1175                1180                1185
Ser Ala Gly Gly Tyr Gly Thr Ser Gly His Asp Ser Thr Ile Ile
        1190                1195                1200
Leu Gln Gln Thr Gly Ala Ser His Ser Ser Val Ser Tyr Arg Ser
        1205                1210                1215
Val Arg Thr Gly Gly Thr Ser Ala Met Ile Gly Ser Ser Gly Tyr
        1220                1225                1230
Gly Gly Ser Ser Ser Ser Arg Ala Met Gly Leu Gly Met Gly Ala
        1235                1240                1245
Ala Gly Leu Ser Met Gly Gly Gly Ser Phe Arg Val Gly Ser Ala
        1250                1255                1260
Gly Ile Gly Gly Met Gly Ile Ser Ser Gly Ile Gly Gly Met Gly
        1265                1270                1275
```

```
Ile Ser Ser Arg Ala Gly Gly Met Ser Ala Tyr Gly Gly Ala Ala
1280            1285                1290

Ser Gly Gly Ala Gly Gly Phe Val Ser Gly Val Pro Met Leu
1295            1300                1305

Gly Tyr Gly Gly Gly Ala Gly Gly Phe Ile Gly Gly Val Ser Pro
1310            1315                1320

Gly Ile Met Ala Ser Pro Ala Phe Thr Ala Gly Arg Ala Ile Thr
1325            1330                1335

Ser Ala Gly Met Ser Gly Val Val Gly Thr Leu Gly Pro Ala Gly
1340            1345                1350

Gly Met Val Pro Ser Leu Val Ser Arg Asp Glu Val Lys Asn Ile
1355            1360                1365

Leu Gly Thr Leu Asn Gln Arg Leu Ala Ser Tyr Val Asp Lys Val
1370            1375                1380

Arg Gln Leu Thr Ile Glu Asn Glu Thr Met Glu Glu Leu Lys
1385            1390                1395

Asn Leu Thr Gly Gly Val Pro Met Ser Pro Asp Ser Thr Val Asn
1400            1405                1410

Leu Glu Asn Val Glu Thr Gln Val Thr Glu Met Leu Thr Glu Val
1415            1420                1425

Ser Asn Leu Thr Leu Glu Arg Val Arg Leu Glu Ile Asp Val Asp
1430            1435                1440

His Leu Arg Ala Thr Ala Asp Glu Ile Lys Ser Lys Tyr Glu Phe
1445            1450                1455

Glu Leu Gly Val Arg Met Gln Leu Glu Thr Asp Ile Ala Asn Met
1460            1465                1470

Lys Arg Asp Leu Glu Ala Ala Asn Asp Met Arg Val Asp Leu Asp
1475            1480                1485

Ser Lys Phe Asn Phe Leu Thr Glu Glu Leu Thr Phe Gln Arg Lys
1490            1495                1500

Thr Gln Met Glu Glu Leu Asn Thr Leu Lys Gln Gln Phe Gly Arg
1505            1510                1515

Leu Gly Pro Val Gln Thr Ser Val Ile Glu Leu Asp Asn Val Lys
1520            1525                1530

Ser Val Asn Leu Thr Asp Ala Leu Asn Val Met Arg Glu Glu Tyr
1535            1540                1545

Gln Gln Val Val Thr Lys Asn Val Gln Glu Ala Glu Thr Tyr Cys
1550            1555                1560

Lys Met Gln Ile Asp Gln Ile Gln Gly Ile Ser Thr Gln Thr Thr
1565            1570                1575

Glu Gln Ile Ser Ile Leu Asp Lys Glu Ile Asn Thr Leu Glu Lys
1580            1585                1590

Glu Leu Gln Pro Leu Asn Val Glu Tyr Gln Arg Leu Leu Thr Thr
1595            1600                1605

Tyr Gln Thr Leu Gly Asp Arg Leu Thr Asp Leu Gln Asn Arg Glu
1610            1615                1620

Ser Ile Asp Leu Val Gln Phe Gln Asn Thr Tyr Thr Arg Tyr Glu
1625            1630                1635

Gln Glu Ile Glu Gly Asn Gln Val Asp Leu Gln Arg Gln Leu Val
1640            1645                1650

Thr Tyr Gln Gln Leu Leu Asp Val Lys Thr Ala Leu Asp Ala Glu
1655            1660                1665
```

```
Ile Ala Thr Tyr Lys Lys Leu Leu Glu Gly Gln Glu Leu Met Val
    1670             1675            1680

Arg Thr Ala Met Ala Asp Asp Phe Ala His Ala Thr Val Val Arg
    1685             1690            1695

Ser Gly Thr Leu Gly Gly Ala Ser Ser Ser Val Gly Tyr Gly
    1700             1705            1710

Ala Ser Ser Thr Thr Leu Gly Ala Ile Ser Gly Gly Tyr Ser Thr
    1715             1720            1725

Gly Gly Gly Ala Ser Tyr Ser Ala Gly Ala Gly Ala Ser Tyr
    1730             1735            1740

Ser Ala Gly Ala Gly Gly Ala Ser Tyr Gly Val Gly Gly Gly Tyr
    1745             1750            1755

Ser Gly Gly Ser Ser Ala Met Met Glu Gly Ser Ser Ser Gly Gly
    1760             1765            1770

His Ser Met Tyr Ser Ser Ser Met Lys Arg Ser Ser Ser Lys
    1775             1780            1785

Ser Ala Ser Ala Ser Ala Gly Gly Tyr Gly Thr Ser Gly His Asp
    1790             1795            1800

Ser Thr Ile Ile Leu Gln Gln
    1805             1810

<210> SEQ ID NO 10
<211> LENGTH: 5263
<212> TYPE: PRT
<213> ORGANISM: Bombyx mori

<400> SEQUENCE: 10

Met Arg Val Lys Thr Phe Val Ile Leu Cys Cys Ala Leu Gln Tyr Val
1               5                   10                  15

Ala Tyr Thr Asn Ala Asn Ile Asn Asp Phe Asp Glu Asp Tyr Phe Gly
                20                  25                  30

Ser Asp Val Thr Val Gln Ser Ser Asn Thr Thr Asp Glu Ile Ile Arg
            35                  40                  45

Asp Ala Ser Gly Ala Val Ile Glu Glu Gln Ile Thr Thr Lys Lys Met
        50                  55                  60

Gln Arg Lys Asn Lys Asn His Gly Ile Leu Gly Lys Asn Glu Lys Met
65                  70                  75                  80

Ile Lys Thr Phe Val Ile Thr Thr Asp Ser Asp Gly Asn Glu Ser Ile
                85                  90                  95

Val Glu Glu Asp Val Leu Met Lys Thr Leu Ser Asp Gly Thr Val Ala
                100                 105                 110

Gln Ser Tyr Val Ala Ala Asp Ala Gly Ala Tyr Ser Gln Ser Gly Pro
            115                 120                 125

Tyr Val Ser Asn Ser Gly Tyr Ser Thr His Gln Gly Tyr Thr Ser Asp
        130                 135                 140

Phe Ser Thr Ser Ala Ala Val Gly Ala Gly Ala Gly Ala Gly Ala Ala
145                 150                 155                 160

Ala Gly Ser Gly Ala Gly Ala Gly Ala Gly Tyr Gly Ala Ala Ser Gly
                165                 170                 175

Ala Gly Ala Gly Ala Gly Ala Gly Ala Gly Tyr Gly Thr Gly
            180                 185                 190

Ala Gly Ala Gly Ala Gly Ala Gly Tyr Gly Ala Gly Ala Gly Ala Gly
        195                 200                 205

Ala Gly Ala Gly Tyr Gly Ala Gly Ala Gly Ala Gly Ala Gly Ala Gly
            210                 215                 220
```

```
Tyr Gly Ala Gly Ala Gly Ala Gly Ala Gly Tyr Gly Ala Gly
225                 230                 235                 240
Ala Gly Ala Gly Ala Gly Ala Gly Tyr Gly Ala Gly Ala Gly
                245                 250                 255
Ala Gly Ala Gly Tyr Gly Ala Ala Ser Gly Ala Gly Ala Gly
                260                 265                 270
Tyr Gly Gln Val Gly Ser Gly Ala Ser Gly Ala Gly Ala Gly
            275                 280                 285
Ala Gly Ala Gly Ser Ala Ala Gly Ser Gly Ala Gly Ala Gly
            290                 295                 300
Thr Gly Ala Gly Ala Gly Tyr Gly Ala Gly Ala Gly Ala Gly
305                 310                 315                 320
Ala Gly Tyr Gly Ala Ala Ser Gly Thr Gly Ala Gly Tyr Gly Ala Gly
                325                 330                 335
Ala Gly Ala Gly Tyr Gly Gly Ala Ser Gly Ala Gly Ala Gly Ala Gly
                340                 345                 350
Ala Gly Ala Gly Ala Gly Ala Gly Ala Gly Tyr Gly Thr Gly Ala Gly
                355                 360                 365
Tyr Gly Ala Gly Ala Gly Ala Gly Ala Gly Ala Gly Ala Gly
370                 375                 380
Tyr Gly Ala Gly Ala Gly Ala Gly Tyr Gly Ala Gly Tyr Gly Val Gly
385                 390                 395                 400
Ala Gly Ala Gly Tyr Gly Ala Gly Tyr Gly Ala Gly Ala Gly Ser Gly
                405                 410                 415
Ala Ala Ser Gly Ala Gly Ser Gly Ala Gly Ser Gly Ala Gly
                420                 425                 430
Ala Gly Ser Gly Ala Gly Ala Gly Ser Gly Ala Gly Ala Gly Ser Gly
            435                 440                 445
Ala Gly Ala Gly Ser Gly Ala Gly Ala Gly Ser Gly Ala Gly Ala Gly
            450                 455                 460
Ser Gly Ala Gly Ala Gly Ser Gly Thr Gly Ala Gly Ser Gly Ala Gly
465                 470                 475                 480
Ala Gly Tyr Gly Ala Gly Ala Gly Ala Gly Tyr Gly Ala Gly Ala Gly
                485                 490                 495
Ser Gly Ala Ala Ser Gly Ala Gly Ala Gly Ser Gly Ala Gly Ala Gly
                500                 505                 510
Ser Gly Ala Gly Ala Gly Ser Gly Ala Gly Ala Gly Ser Gly Ala Gly
            515                 520                 525
Ala Gly Ser Gly Ala Gly Ala Gly Tyr Gly Ala Gly Ala Gly Ala Gly
            530                 535                 540
Tyr Gly Ala Gly Ala Gly Ala Gly Tyr Gly Ala Gly Ala Gly Val Gly
545                 550                 555                 560
Tyr Gly Ala Gly Ala Gly Ser Gly Ala Ala Ser Gly Ala Gly Ala Gly
                565                 570                 575
Ser Gly Ala Gly Ala Gly Ser Gly Ala Gly Ala Gly Ser Gly Ala Gly
                580                 585                 590
Ala Gly Ser Gly Ala Gly Ala Gly Ser Gly Ala Gly Ala Gly Ser Gly
            595                 600                 605
Ala Gly Ala Gly Ser Gly Ala Gly Ala Gly Ser Gly Ala Gly Ala Gly
            610                 615                 620
Ser Gly Ala Gly Val Gly Tyr Gly Ala Gly Val Gly Ala Gly Tyr Gly
625                 630                 635                 640
```

```
Ala Gly Tyr Gly Ala Gly Ala Gly Ala Gly Tyr Gly Ala Gly Ala Gly
            645                 650                 655

Ser Gly Ala Ala Ser Gly Ala Gly Ala Gly Ala Gly Ala Gly
        660                 665                 670

Thr Gly Ser Ser Gly Phe Gly Pro Tyr Val Ala Asn Gly Gly Tyr Ser
        675                 680                 685

Arg Ser Asp Gly Tyr Glu Tyr Ala Trp Ser Ser Asp Phe Gly Thr Gly
    690                 695                 700

Ser Gly Ala Gly Ala Gly Ser Gly Ala Gly Ala Gly Ser Gly Ala Gly
705                 710                 715                 720

Ala Gly Ser Gly Ala Gly Ala Gly Ser Gly Ala Gly Ala Gly Ser Gly
                725                 730                 735

Ala Gly Ala Gly Tyr Gly Ala Gly Val Gly Val Gly Tyr Gly Ala Gly
            740                 745                 750

Tyr Gly Ala Gly Ala Gly Ala Gly Tyr Gly Ala Gly Ala Gly Ser Gly
        755                 760                 765

Ala Ala Ser Gly Ala Gly Ala Gly Ser Gly Ala Gly Ala Gly Ser Gly
        770                 775                 780

Ala Gly Ala Gly Ser Gly Ala Gly Ala Gly Ser Gly Ala Gly Ala Gly
785                 790                 795                 800

Ser Gly Ala Gly Ala Gly Ser Gly Ala Gly Ala Gly Ser Gly Ala Gly
                805                 810                 815

Ala Gly Ser Gly Ala Gly Ala Gly Ser Gly Ala Gly Ala Gly Ser Gly
            820                 825                 830

Ala Gly Val Gly Ser Gly Ala Gly Ala Gly Ser Gly Ala Gly Ala Gly
        835                 840                 845

Val Gly Tyr Gly Ala Gly Ala Gly Val Gly Tyr Gly Ala Gly Ala Gly
    850                 855                 860

Ser Gly Ala Ala Ser Gly Ala Gly Ala Gly Ser Gly Ala Gly Ala Gly
865                 870                 875                 880

Ser Gly Ala Gly Ala Gly Ser Gly Ala Gly Ala Gly Ser Gly Ala Gly
                885                 890                 895

Ala Gly Ser Gly Ala Gly Ala Gly Ser Gly Ala Gly Ala Gly Ser Gly
            900                 905                 910

Ala Gly Ala Gly Ser Gly Ala Gly Ala Gly Ser Gly Ala Gly Val Gly
        915                 920                 925

Tyr Gly Ala Gly Val Gly Ala Gly Tyr Gly Ala Gly Tyr Gly Ala Gly
    930                 935                 940

Ala Gly Ala Gly Tyr Gly Ala Gly Ala Gly Ser Gly Ala Ala Ser Gly
945                 950                 955                 960

Ala Gly Ala Gly Ser Gly Ala Gly Ala Gly Ser Gly Ala Gly Ala Gly
                965                 970                 975

Ser Gly Ala Gly Ala Gly Ser Gly Ala Gly Ala Gly Ser Gly Ala Gly
            980                 985                 990

Ala Gly Ser Gly Ala Gly Ala Gly Ser Gly Ala Gly Ala Gly Ser Gly
        995                 1000                1005

Ala Gly Ala Gly Ser Gly Ala Gly Ala Gly Ser Gly Ala Gly Ala
    1010                1015                1020

Gly Ser Gly Ala Gly Ala Gly Tyr Gly Ala Gly Ala Gly Ala Gly
    1025                1030                1035

Tyr Gly Ala Gly Tyr Gly Ala Gly Ala Gly Ala Gly Tyr Gly Ala
    1040                1045                1050

Gly Ala Gly Ser Gly Ala Ala Ser Gly Ala Gly Ser Gly Ala Gly
```

-continued

```
            1055                1060                1065
Ala Gly Ser Gly Ala Gly Ala Gly Ala Gly Ser Gly Ala Gly Ala
            1070                1075                1080
Gly Ser Gly Ala Gly Ala Gly Ser Gly Ala Gly Ala Gly Ser Gly
            1085                1090                1095
Ala Gly Ala Gly Ser Gly Ala Gly Ala Gly Ser Gly Ala Gly Ala
            1100                1105                1110
Gly Tyr Gly Ala Gly Val Gly Ala Gly Tyr Gly Ala Gly Tyr Gly
            1115                1120                1125
Ala Gly Ala Gly Ala Gly Tyr Gly Ala Gly Ala Gly Ser Gly Ala
            1130                1135                1140
Ala Ser Gly Ala Gly Ala Gly Ser Gly Ala Gly Ala Gly Ser Gly
            1145                1150                1155
Ala Gly Ala Gly Ser Gly Ala Gly Ala Gly Ser Gly Ala Gly Ala
            1160                1165                1170
Gly Ser Gly Ala Gly Ala Gly Ser Gly Ala Gly Ala Gly Ser Gly
            1175                1180                1185
Ala Gly Val Gly Tyr Gly Ala Gly Tyr Gly Ala Gly Ala Gly Ala
            1190                1195                1200
Gly Tyr Gly Ala Gly Ala Gly Ser Gly Ala Ala Ser Gly Ala Gly
            1205                1210                1215
Ala Gly Ala Gly Ala Gly Ala Gly Thr Gly Ser Ser Gly Phe Gly
            1220                1225                1230
Pro Tyr Val Ala His Gly Gly Tyr Ser Gly Tyr Glu Tyr Ala Trp
            1235                1240                1245
Ser Ser Glu Ser Asp Phe Gly Thr Gly Ser Gly Ala Gly Ala Gly
            1250                1255                1260
Ser Gly Ala Gly Ala Gly Ser Gly Ala Gly Ala Gly Ser Gly Ala
            1265                1270                1275
Gly Ala Gly Ser Gly Ala Gly Tyr Gly Ala Gly Val Gly Ala Gly
            1280                1285                1290
Tyr Gly Ala Gly Tyr Gly Ala Gly Ala Gly Ala Gly Tyr Gly Ala
            1295                1300                1305
Gly Ala Gly Ser Gly Ala Gly Ser Gly Ala Gly Ala Gly Ser Gly
            1310                1315                1320
Ala Gly Ala Gly Ser Gly Ala Gly Ala Gly Ser Gly Ala Gly Ala
            1325                1330                1335
Gly Ser Gly Ala Gly Ala Gly Ser Gly Ala Gly Ala Gly Ser Gly
            1340                1345                1350
Ala Gly Ala Gly Ser Gly Ala Gly Ala Gly Ser Gly Ala Gly Ala
            1355                1360                1365
Gly Tyr Gly Ala Gly Tyr Gly Ala Gly Ala Gly Ala Gly Tyr Gly
            1370                1375                1380
Ala Gly Ala Gly Ser Gly Ala Gly Ser Gly Ala Gly Ala Gly Ser
            1385                1390                1395
Gly Ala Gly Ala Gly Ser Gly Ala Gly Ala Gly Ser Gly Ala Gly
            1400                1405                1410
Ala Gly Ser Gly Ala Gly Ala Gly Ser Gly Ala Gly Ala Gly Ser
            1415                1420                1425
Gly Ala Gly Ala Gly Ser Gly Ala Gly Ala Gly Tyr Gly Ala Gly
            1430                1435                1440
Val Gly Ala Gly Tyr Gly Ala Gly Tyr Gly Ala Gly Ala Gly Ala
            1445                1450                1455
```

-continued

Gly Tyr Gly Ala Gly Ala Gly Ser Gly Ala Ser Gly Ala Gly
    1460            1465            1470

Ala Gly Ser Gly Ala Gly Ala Gly Ser Gly Ala Gly Ala Gly Ser
    1475            1480            1485

Gly Ala Gly Val Gly Ser Gly Ala Gly Ala Gly Ser Gly Ala Gly
    1490            1495            1500

Ala Gly Ser Gly Ala Gly Ala Gly Ser Gly Ala Gly Ala Gly Tyr
    1505            1510            1515

Gly Ala Gly Tyr Gly Ala Gly Ala Gly Ala Gly Tyr Gly Ala Gly
    1520            1525            1530

Ala Gly Ser Gly Ala Gly Ser Gly Ala Gly Ala Gly Ser Gly Ala
    1535            1540            1545

Gly Ala Gly Ser Gly Ala Gly Ala Gly Ser Gly Ala Gly Ala Gly
    1550            1555            1560

Ser Gly Ala Gly Ala Gly Ser Gly Ala Gly Ala Gly Ser Gly Ala
    1565            1570            1575

Gly Ala Gly Ser Gly Ala Gly Val Gly Tyr Gly Ala Gly Val Gly
    1580            1585            1590

Ala Gly Tyr Gly Ala Gly Tyr Gly Ala Gly Ala Gly Ala Gly Tyr
    1595            1600            1605

Gly Ala Gly Ala Gly Ser Gly Ala Ala Ser Gly Ala Gly Ala Gly
    1610            1615            1620

Ala Gly Ala Gly Ala Gly Thr Gly Ser Ser Gly Phe Gly Pro Tyr
    1625            1630            1635

Val Ala Asn Gly Gly Tyr Ser Gly Tyr Glu Tyr Ala Trp Ser Ser
    1640            1645            1650

Glu Ser Asp Phe Gly Thr Gly Ser Gly Ala Gly Ala Gly Ser Gly
    1655            1660            1665

Ala Gly Ala Gly Ser Gly Ala Gly Ala Gly Ser Gly Ala Gly Ala
    1670            1675            1680

Gly Ser Gly Ala Gly Ala Gly Tyr Gly Ala Gly Tyr Gly Ala Gly
    1685            1690            1695

Ala Gly Ala Gly Tyr Gly Ala Gly Ala Gly Ser Gly Ala Gly Ser
    1700            1705            1710

Gly Ala Gly Ala Gly Ser Gly Ala Gly Ala Gly Ser Gly Ala Gly
    1715            1720            1725

Ala Gly Ser Gly Ala Gly Ala Gly Ser Gly Ala Gly Ala Gly Ser
    1730            1735            1740

Gly Ala Gly Ala Gly Ser Gly Ala Gly Ala Gly Ser Gly Ala Gly
    1745            1750            1755

Ser Gly Ser Gly Ala Gly Ala Gly Ser Gly Ala Gly Ala Gly Ser
    1760            1765            1770

Gly Ala Gly Ala Gly Tyr Gly Ala Gly Val Gly Ala Gly Tyr Gly
    1775            1780            1785

Val Gly Tyr Gly Ala Gly Ala Gly Ala Gly Tyr Gly Ala Gly Ala
    1790            1795            1800

Gly Ser Gly Ala Ala Ser Gly Ala Gly Ala Gly Ala Gly Ala Gly
    1805            1810            1815

Ala Gly Thr Gly Ser Ser Gly Phe Gly Pro Tyr Val Ala His Gly
    1820            1825            1830

Gly Tyr Ser Gly Tyr Glu Tyr Ala Trp Ser Ser Glu Ser Asp Phe
    1835            1840            1845

Gly Thr Gly Ser Gly Ala Gly Ala Gly Ser Gly Ala Gly Ala Gly
    1850                1855                1860

Ser Gly Ala Gly Ala Gly Ser Gly Ala Gly Ala Gly Ser Gly Ala
    1865                1870                1875

Gly Ala Gly Ser Gly Ala Gly Ala Gly Ser Gly Ala Gly Ala Gly
    1880                1885                1890

Tyr Gly Ala Gly Val Gly Ala Gly Tyr Gly Ala Ala Tyr Gly Ala
    1895                1900                1905

Gly Ala Gly Ala Gly Tyr Gly Ala Gly Ala Gly Ser Gly Ala Ala
    1910                1915                1920

Ser Gly Ala Gly Ala Gly Ser Gly Ala Gly Ala Gly Ser Gly Ala
    1925                1930                1935

Gly Ala Gly Ser Gly Ala Gly Ala Gly Ser Gly Ala Gly Ala Gly
    1940                1945                1950

Ser Gly Ala Gly Ala Gly Ser Gly Ala Gly Ala Gly Ser Gly Ala
    1955                1960                1965

Gly Ala Gly Ser Gly Ala Gly Ala Gly Ser Gly Ala Gly Ala Gly
    1970                1975                1980

Ser Gly Ala Gly Ala Gly Tyr Gly Ala Gly Ala Gly Ala Gly Tyr
    1985                1990                1995

Gly Ala Gly Ala Gly Ser Gly Ala Gly Ser Gly Ala Gly Ala Gly
    2000                2005                2010

Ser Gly Ala Gly Ala Gly Ser Gly Ala Gly Ala Gly Ser Gly Ala
    2015                2020                2025

Gly Ala Gly Ser Gly Ala Gly Ala Gly Ser Gly Ala Gly Ser Gly
    2030                2035                2040

Ser Gly Ala Gly Ala Gly Ser Gly Ala Gly Ala Gly Ser Gly Ala
    2045                2050                2055

Gly Ala Gly Tyr Gly Ala Gly Val Gly Ala Gly Tyr Gly Ala Gly
    2060                2065                2070

Tyr Gly Ala Gly Ala Gly Ala Gly Tyr Gly Ala Gly Ala Gly Ser
    2075                2080                2085

Gly Ala Gly Ser Gly Ala Gly Ala Gly Ser Gly Ala Gly Ala Gly
    2090                2095                2100

Tyr Gly Ala Gly Ala Gly Ala Gly Tyr Gly Ala Gly Tyr Gly Ala
    2105                2110                2115

Gly Ala Gly Ala Gly Tyr Gly Ala Gly Ala Gly Thr Gly Ala Gly
    2120                2125                2130

Ser Gly Ala Gly Ala Gly Ser Gly Ala Gly Ala Gly Ser Gly Ala
    2135                2140                2145

Gly Ala Gly Ser Gly Ala Gly Ala Gly Ser Gly Ala Gly Ala Gly
    2150                2155                2160

Ser Gly Ala Gly Ala Gly Ser Gly Ala Gly Ser Gly Ser Gly Ala
    2165                2170                2175

Gly Ala Gly Ser Gly Ala Gly Ala Gly Ser Gly Ala Gly Ala Gly
    2180                2185                2190

Ser Gly Ala Gly Ala Gly Ser Gly Ala Gly Ala Gly Ser Gly Ala
    2195                2200                2205

Gly Ala Gly Tyr Gly Ala Gly Ala Gly Ala Gly Tyr Gly Ala Gly
    2210                2215                2220

Tyr Gly Ala Gly Ala Gly Ala Gly Tyr Gly Ala Gly Ala Gly Ser
    2225                2230                2235

Gly Ala Gly Ser Gly Ala Gly Ala Gly Ser Gly Ala Gly Ala Gly

-continued

```
             2240                2245                2250
Ser Gly Ala Gly Ala Gly  Ser Gly Ala Gly  Tyr Gly Ala
         2255                2260                2265
Gly Tyr Gly Ala Gly Ala  Gly Ser Gly Ala Ala Ser  Gly Ala Gly
         2270                2275                2280
Ala Gly Ala Gly Ala Gly Ala  Gly Thr Gly Ser Ser  Gly Phe Gly
         2285                2290                2295
Pro Tyr Val Ala His Gly Gly  Tyr Ser Gly Tyr Glu  Tyr Ala Trp
         2300                2305                2310
Ser Ser Glu Ser Asp Phe Gly  Thr Gly Ser Gly Ala  Gly Ala Gly
         2315                2320                2325
Ser Gly Ala Gly Ala Gly Ala  Gly Ala Gly Ala Gly  Ser Gly Ala
         2330                2335                2340
Gly Ala Gly Tyr Gly Ala Gly  Val Gly Ala Gly Tyr  Gly Ala Gly
         2345                2350                2355
Tyr Gly Ala Gly Ala Gly Ala  Gly Tyr Gly Ala Gly  Ala Gly Ser
         2360                2365                2370
Gly Thr Gly Ser Gly Ala Gly  Ala Gly Ser Gly Ala  Gly Ala Gly
         2375                2380                2385
Tyr Gly Ala Gly Val Gly Ala  Gly Tyr Gly Ala Gly  Ala Gly Ser
         2390                2395                2400
Gly Ala Ala Phe Gly Ala Gly  Ala Gly Ala Gly Ala  Gly Ser Gly
         2405                2410                2415
Ala Gly Ala Gly Ser Gly Ala  Gly Ala Gly Ser Gly  Ala Gly Ala
         2420                2425                2430
Gly Ser Gly Ala Gly Ala Gly  Ser Gly Ala Gly Ala  Gly Tyr Gly
         2435                2440                2445
Ala Gly Tyr Gly Ala Gly Val  Gly Ala Gly Tyr Gly  Ala Gly Ala
         2450                2455                2460
Gly Ser Gly Ala Ala Ser Gly  Ala Gly Ala Gly Ser  Gly Ala Gly
         2465                2470                2475
Ala Gly Ser Gly Ala Gly Ala  Gly Ser Gly Ala Gly  Ala Gly Ser
         2480                2485                2490
Gly Ala Gly Ala Gly Ser Gly  Ala Gly Ala Gly Tyr  Gly Ala Gly
         2495                2500                2505
Val Gly Ala Gly Tyr Gly Ala  Gly Tyr Gly Ala Gly  Ala Gly Ala
         2510                2515                2520
Gly Tyr Gly Ala Gly Ala Gly  Ser Gly Ala Ala Ser  Gly Ala Gly
         2525                2530                2535
Ala Gly Ser Gly Ala Gly Ala  Gly Ala Gly Ser Gly  Ala Gly Ala
         2540                2545                2550
Gly Ser Gly Ala Gly Ala Gly  Ser Gly Ala Gly Ala  Gly Ser Gly
         2555                2560                2565
Ala Gly Ser Gly Ala Gly Ala  Gly Ser Gly Ala Gly  Ala Gly Ser
         2570                2575                2580
Gly Ala Gly Ala Gly Tyr Gly  Ala Gly Ala Gly Ser  Gly Ala Ala
         2585                2590                2595
Ser Gly Ala Gly Ala Gly Ala  Gly Ala Gly Ala Gly  Thr Gly Ser
         2600                2605                2610
Ser Gly Phe Gly Pro Tyr Val  Ala Asn Gly Gly Tyr  Ser Gly Tyr
         2615                2620                2625
Glu Tyr Ala Trp Ser Ser Glu  Ser Asp Phe Gly Thr  Gly Ser Gly
         2630                2635                2640
```

Ala Gly  Ala Gly Ser Gly Ala  Gly Ala Gly Ser Gly  Ala Gly Ala
    2645                2650                 2655

Gly Ser  Gly Ala Gly Ala Gly  Ser Gly Ala Gly Ala  Gly Tyr Gly
    2660                2665                 2670

Ala Gly  Val Gly Ala Gly Tyr  Gly Ala Gly Tyr Gly  Ala Gly Ala
    2675                2680                 2685

Gly Ala  Gly Tyr Gly Ala Gly  Ala Gly Ser Gly Ala  Gly Ser Gly
    2690                2695                 2700

Ala Gly  Ala Gly Ser Gly Ala  Gly Ala Gly Ser Gly  Ala Gly Ala
    2705                2710                 2715

Gly Ser  Gly Ala Gly Ala Gly  Ser Gly Ala Gly Ala  Gly Ser Gly
    2720                2725                 2730

Ala Gly  Ala Gly Ser Gly Ala  Gly Ala Gly Tyr Gly  Ala Gly Ala
    2735                2740                 2745

Gly Ser  Gly Ala Ala Ser Gly  Ala Gly Ala Gly Ser  Gly Ala Gly
    2750                2755                 2760

Ala Gly  Ser Gly Ala Gly Ala  Gly Ser Gly Ala Gly  Ala Gly Ser
    2765                2770                 2775

Gly Ala  Gly Ala Gly Ser Gly  Ala Gly Ala Gly Ser  Gly Ala Gly
    2780                2785                 2790

Ala Gly  Tyr Gly Ala Gly Val  Gly Ala Gly Tyr Gly  Val Gly Tyr
    2795                2800                 2805

Gly Ala  Gly Ala Gly Ala Gly  Tyr Gly Ala Gly Ala  Gly Ser Gly
    2810                2815                 2820

Ala Gly  Ser Gly Ala Gly Ala  Gly Ser Gly Ala Gly  Ala Gly Ser
    2825                2830                 2835

Gly Ala  Gly Ala Gly Ser Gly  Ala Gly Ala Gly Ser  Gly Ala Gly
    2840                2845                 2850

Ser Gly  Ala Gly Ala Gly Ser  Gly Ala Gly Ala Gly  Ser Gly Ala
    2855                2860                 2865

Gly Ala  Gly Ser Gly Ala Gly  Ser Gly Ala Gly Ala  Gly Ser Gly
    2870                2875                 2880

Ala Gly  Ala Gly Tyr Gly Val  Gly Tyr Gly Ala Gly  Ala Gly Ala
    2885                2890                 2895

Gly Tyr  Gly Ala Gly Ala Gly  Ser Gly Ala Gly Ser  Gly Ala Gly
    2900                2905                 2910

Ala Gly  Ser Gly Ala Gly Ala  Gly Ser Gly Ala Gly  Ala Gly Ser
    2915                2920                 2925

Gly Ala  Gly Ser Gly Ala Gly  Ala Gly Ser Gly Ala  Gly Ala Gly
    2930                2935                 2940

Ser Gly  Ala Gly Ala Gly Ser  Gly Ala Gly Ala Gly  Tyr Gly Ala
    2945                2950                 2955

Gly Val  Gly Ala Gly Tyr Gly  Val Gly Tyr Gly Ala  Gly Ala Gly
    2960                2965                 2970

Ala Gly  Tyr Gly Ala Gly Ala  Gly Ser Gly Ala Gly  Ser Gly Ala
    2975                2980                 2985

Gly Ala  Gly Ser Gly Ala Gly  Ala Gly Ser Gly Ala  Gly Ala Gly
    2990                2995                 3000

Ser Gly  Ala Gly Ala Gly Ser  Gly Ala Gly Ala Gly  Ser Gly Ala
    3005                3010                 3015

Gly Ala  Gly Ser Gly Ala Gly  Ala Gly Ser Gly Ala  Gly Ser Gly
    3020                3025                 3030

```
Ala Gly Ala Gly Ser Gly Ala Gly Ala Gly Ala Gly Ala
    3035                3040                3045

Gly Ser Gly Ala Gly Ala Gly Ser Gly Ala Gly Ser Gly Ala Gly
    3050                3055                3060

Ala Gly Ser Gly Ala Gly Ala Gly Ser Gly Ala Gly Ala Gly Ser
    3065                3070                3075

Gly Ala Gly Ala Gly Tyr Gly Ala Gly Val Gly Ala Gly Tyr Gly
    3080                3085                3090

Val Gly Tyr Gly Ala Gly Val Gly Ala Gly Tyr Gly Ala Gly Ala
    3095                3100                3105

Gly Ser Gly Ala Ala Ser Gly Ala Gly Ala Gly Ser Gly Ala Gly
    3110                3115                3120

Ala Gly Ala Gly Ser Gly Ala Gly Ala Gly Ser Gly Ala Gly Ala
    3125                3130                3135

Gly Ser Gly Ala Gly Ala Gly Ser Gly Ala Gly Ala Gly Ser Gly
    3140                3145                3150

Ala Gly Ala Gly Ser Gly Ala Gly Ala Gly Tyr Gly Ala Gly Tyr
    3155                3160                3165

Gly Ala Gly Val Gly Ala Gly Tyr Gly Ala Gly Ala Gly Val Gly
    3170                3175                3180

Tyr Gly Ala Gly Ala Gly Ala Gly Tyr Gly Ala Gly Ala Gly Ser
    3185                3190                3195

Gly Ala Ala Ser Gly Ala Gly Ala Gly Ala Gly Ser Gly Ala Gly
    3200                3205                3210

Ala Gly Thr Gly Ala Gly Ala Gly Ser Gly Ala Gly Ala Gly Tyr
    3215                3220                3225

Gly Ala Gly Ala Gly Ser Gly Ala Ala Ser Gly Ala Gly Ala Gly
    3230                3235                3240

Ala Gly Ala Gly Ala Gly Thr Gly Ser Ser Gly Phe Gly Pro Tyr
    3245                3250                3255

Val Ala Asn Gly Gly Tyr Ser Gly Tyr Glu Tyr Ala Trp Ser Ser
    3260                3265                3270

Glu Ser Asp Phe Gly Thr Gly Ser Gly Ala Gly Ala Gly Ser Gly
    3275                3280                3285

Ala Gly Ala Gly Ser Gly Ala Gly Ala Gly Ser Gly Ala Gly Ala
    3290                3295                3300

Gly Ser Gly Ala Gly Ala Gly Tyr Gly Ala Gly Val Gly Ala Gly
    3305                3310                3315

Tyr Gly Ala Gly Ala Gly Ser Gly Ala Gly Ser Gly Ala Gly Ala
    3320                3325                3330

Gly Ser Gly Ala Gly Ala Gly Ser Gly Ala Gly Ala Gly Ser Gly
    3335                3340                3345

Ala Gly Ala Gly Ser Gly Ala Gly Ala Gly Tyr Gly Ala Gly Ala
    3350                3355                3360

Gly Ser Gly Thr Gly Ser Gly Ala Gly Ala Gly Ser Gly Ala Gly
    3365                3370                3375

Ala Gly Ser Gly Ala Gly Ala Gly Ser Gly Ala Gly Ala Gly Ser
    3380                3385                3390

Gly Ala Gly Ala Gly Ser Gly Ala Gly Ala Gly Ser Gly Val Gly
    3395                3400                3405

Ala Gly Tyr Gly Val Gly Tyr Gly Ala Gly Ala Gly Ala Gly Tyr
    3410                3415                3420

Gly Val Gly Tyr Gly Ala Gly Ala Gly Ala Gly Tyr Gly Ala Gly
```

```
            3425                3430                3435
Ala Gly Ser Gly Thr Gly Ser  Gly Ala Gly Ala  Gly Ser Gly Ala
        3440                3445                3450
Gly Ala Gly Ser Gly Ala Gly  Ala Gly Ser Gly  Ala Gly Ala Gly
        3455                3460                3465
Ser Gly Ala Gly Ala Gly Ser  Gly Ala Gly Ala  Gly Ser Gly Ala
        3470                3475                3480
Gly Ala Gly Tyr Gly Ala Gly  Val Gly Ala Gly  Tyr Gly Val Gly
        3485                3490                3495
Tyr Gly Ala Gly Ala Gly Ala  Gly Tyr Gly Ala  Gly Ala Gly Ser
        3500                3505                3510
Gly Ala Gly Ser Gly Ala Gly  Ala Gly Ser Gly  Ala Gly Ala Gly
        3515                3520                3525
Ser Gly Ala Gly Ala Gly Ser  Gly Ala Gly Ala  Gly Ser Gly Ala
        3530                3535                3540
Gly Ser Gly Ala Gly Ala Gly  Ser Gly Ala Gly  Ala Gly Ser Gly
        3545                3550                3555
Ala Gly Ala Gly Ser Gly Ala  Gly Ser Gly Ala  Gly Ala Gly Ser
        3560                3565                3570
Gly Ala Gly Ala Gly Tyr Gly  Val Gly Tyr Gly  Ala Gly Ala Gly
        3575                3580                3585
Ala Gly Tyr Gly Ala Gly Ala  Gly Ser Gly Ala  Gly Ser Gly Ala
        3590                3595                3600
Gly Ala Gly Ser Gly Ala Gly  Ala Gly Ser Gly  Ala Gly Ala Gly
        3605                3610                3615
Ser Gly Ala Gly Ser Gly Ala  Gly Ala Gly Ser  Gly Ala Gly Ala
        3620                3625                3630
Gly Ser Gly Ala Gly Ala Gly  Ser Gly Ala Gly  Ala Gly Tyr Gly
        3635                3640                3645
Ala Gly Val Gly Ala Gly Tyr  Gly Val Gly Tyr  Gly Ala Gly Ala
        3650                3655                3660
Gly Ala Gly Tyr Gly Ala Gly  Ala Gly Ser Gly  Ala Gly Ser Gly
        3665                3670                3675
Ala Gly Ala Gly Ser Gly Ala  Gly Ala Gly Ser  Gly Ala Gly Ala
        3680                3685                3690
Gly Ser Gly Ala Gly Ala Gly  Ser Gly Ala Gly  Ala Gly Ser Gly
        3695                3700                3705
Ala Gly Ala Gly Ser Gly Ala  Gly Ala Gly Ser  Gly Ala Gly Ser
        3710                3715                3720
Gly Ala Gly Ala Gly Ser Gly  Ala Gly Ala Gly  Ser Gly Ala Gly
        3725                3730                3735
Ala Gly Ser Gly Ala Gly Ala  Gly Tyr Gly Ala  Gly Val Gly Ala
        3740                3745                3750
Gly Tyr Gly Val Gly Tyr Gly  Ala Gly Ala Gly  Ala Gly Tyr Gly
        3755                3760                3765
Ala Gly Ala Gly Ser Gly Ala  Ala Ser Gly Ala  Gly Ala Gly Ala
        3770                3775                3780
Gly Ala Gly Ala Gly Thr Gly  Ser Ser Gly Phe  Gly Pro Tyr Val
        3785                3790                3795
Ala Asn Gly Gly Tyr Ser Gly  Tyr Glu Tyr Ala  Trp Ser Ser Glu
        3800                3805                3810
Ser Asp Phe Gly Thr Gly Ser  Gly Ala Gly Ala  Gly Ser Gly Ala
        3815                3820                3825
```

```
Gly Ala Gly Ser Gly Ala Gly Ala Gly Tyr Gly Ala Gly Tyr Gly
            3830             3835                 3840

Ala Gly Val Gly Ala Gly Tyr Gly Ala Gly Ala Gly Val Gly Tyr
            3845             3850                 3855

Gly Ala Gly Ala Gly Ala Gly Tyr Gly Ala Gly Ala Gly Ser Gly
            3860             3865                 3870

Ala Ala Ser Gly Ala Gly Ala Gly Ala Gly Ala Gly Ala Gly Ser
            3875             3880                 3885

Gly Ala Gly Ala Gly Ser Gly Ala Gly Ala Gly Ala Gly Ser Gly
            3890             3895                 3900

Ala Gly Ala Gly Tyr Gly Ala Gly Tyr Gly Ile Gly Val Gly Ala
            3905             3910                 3915

Gly Tyr Gly Ala Gly Ala Gly Val Gly Tyr Gly Ala Gly Ala Gly
            3920             3925                 3930

Ala Gly Tyr Gly Ala Gly Ala Gly Ser Gly Ala Ala Ser Gly Ala
            3935             3940                 3945

Gly Ala Gly Ser Gly Ala Gly Ala Gly Ser Gly Ala Gly Ala Gly
            3950             3955                 3960

Ser Gly Ala Gly Ala Gly Ser Gly Ala Gly Ala Gly Ser Gly Ala
            3965             3970                 3975

Gly Ala Gly Ser Gly Ala Gly Ala Gly Tyr Gly Ala Gly Tyr Gly
            3980             3985                 3990

Ala Gly Val Gly Ala Gly Tyr Gly Ala Gly Ala Gly Val Gly Tyr
            3995             4000                 4005

Gly Ala Gly Ala Gly Ala Gly Tyr Gly Ala Gly Ala Gly Ser Gly
            4010             4015                 4020

Ala Ala Ser Gly Ala Gly Ala Gly Ala Gly Ala Gly Ala Gly Ala
            4025             4030                 4035

Gly Ser Gly Ala Gly Ala Gly Ser Gly Ala Gly Ala Gly Ser Gly
            4040             4045                 4050

Ala Gly Ala Gly Ser Gly Ala Gly Ala Gly Ser Gly Ala Gly Ala
            4055             4060                 4065

Gly Ser Gly Ala Gly Ala Gly Ser Gly Ala Gly Ala Gly Ser Gly
            4070             4075                 4080

Ala Gly Ala Gly Ser Gly Ala Gly Ala Gly Tyr Gly Ala Gly Val
            4085             4090                 4095

Gly Ala Gly Tyr Gly Ala Gly Tyr Gly Gly Ala Gly Ala Gly Tyr
            4100             4105                 4110

Gly Ala Gly Ala Gly Ser Gly Ala Ala Ser Gly Ala Gly Ala Gly
            4115             4120                 4125

Ser Gly Ala Gly Ala Gly Ser Gly Ala Gly Ala Gly Ser Gly Ala
            4130             4135                 4140

Gly Ala Gly Ser Gly Ala Gly Ala Gly Ser Gly Ala Gly Ala Gly
            4145             4150                 4155

Tyr Gly Ala Gly Ala Gly Ser Gly Ala Ala Ser Gly Ala Gly Ala
            4160             4165                 4170

Gly Ala Gly Ala Gly Ala Gly Thr Gly Ser Ser Gly Phe Gly Pro
            4175             4180                 4185

Tyr Val Asn Gly Gly Tyr Ser Gly Tyr Glu Tyr Ala Trp Ser Ser
            4190             4195                 4200

Glu Ser Asp Phe Gly Thr Gly Ser Gly Ala Gly Ala Gly Ser Gly
            4205             4210                 4215
```

```
Ala Gly  Ala Gly Ser Gly Ala  Gly Ala Gly Tyr  Gly  Ala Gly Val
    4220             4225              4230

Gly Ala  Gly Tyr Gly Ala Gly  Tyr Gly Ala Gly  Ala  Gly Ala Gly
    4235             4240              4245

Tyr Gly  Ala Gly Ala Gly Ser  Gly Ala Ala Ser  Gly  Ala Gly Ala
    4250             4255              4260

Gly Ser  Gly Ala Gly Ala Gly  Ser Gly Ala Gly  Ala  Gly Ser Gly
    4265             4270              4275

Ala Gly  Ala Gly Ser Gly Ala  Gly Ser Gly Ala  Gly  Ala Gly Ser
    4280             4285              4290

Gly Ala  Gly Ala Gly Ser Gly  Ala Gly Ala Gly  Ser  Gly Ala Gly
    4295             4300              4305

Ala Gly  Ser Gly Ala Gly Ala  Gly Ser Gly Ala  Gly  Ala Gly Tyr
    4310             4315              4320

Gly Ala  Gly Val Gly Ala Gly  Tyr Gly Ala Gly  Tyr  Gly Ala Gly
    4325             4330              4335

Ala Gly  Ala Gly Tyr Gly Ala  Gly Ala Gly Ser  Gly  Ala Ala Ser
    4340             4345              4350

Gly Ala  Gly Ala Gly Ser Gly  Ala Gly Ala Gly  Ala  Gly Ser Gly
    4355             4360              4365

Ala Gly  Ala Gly Ser Gly Ala  Gly Ala Gly Ser  Gly  Ala Gly Ala
    4370             4375              4380

Gly Ser  Gly Ala Ala Gly Ser  Gly Ala Gly Ala  Gly  Ser Gly
    4385             4390              4395

Ala Gly  Ser Gly Ala Gly Ala  Gly Ser Gly Ala  Gly  Ala Gly Tyr
    4400             4405              4410

Gly Ala  Gly Tyr Gly Ala Gly  Val Gly Ala Gly  Tyr  Gly Ala Gly
    4415             4420              4425

Ala Gly  Val Gly Tyr Gly Ala  Gly Ala Gly Ala  Gly  Tyr Gly Ala
    4430             4435              4440

Gly Ala  Gly Ser Gly Ala Ala  Ser Gly Ala Gly  Ala  Gly Ser Gly
    4445             4450              4455

Ser Gly  Ala Gly Ser Gly Ala  Gly Ala Gly Ser  Gly  Ala Gly Ala
    4460             4465              4470

Gly Ser  Gly Ala Gly Ala Gly  Ala Gly Ser Gly  Ala  Gly Ala Gly
    4475             4480              4485

Ser Gly  Ala Gly Ala Gly Ser  Gly Ala Gly Ala  Gly  Tyr Gly Ala
    4490             4495              4500

Gly Tyr  Gly Ala Gly Ala Gly  Ser Gly Ala Ala  Ser  Gly Ala Gly
    4505             4510              4515

Ala Gly  Ala Gly Ala Gly Ala  Gly Thr Gly Ser  Ser  Gly Phe Gly
    4520             4525              4530

Pro Tyr  Val Ala Asn Gly Gly  Tyr Ser Gly Tyr  Glu  Tyr Ala Trp
    4535             4540              4545

Ser Ser  Glu Ser Asp Phe Gly  Thr Gly Ser Gly  Ala  Gly Ala Gly
    4550             4555              4560

Ser Gly  Ala Gly Ala Gly Ser  Gly Ala Gly Ala  Gly  Tyr Gly Ala
    4565             4570              4575

Gly Val  Gly Ala Gly Tyr Gly  Ala Gly Tyr Gly  Ala  Gly Ala Gly
    4580             4585              4590

Ala Gly  Tyr Gly Ala Gly Ala  Gly Ser Gly Ala  Gly  Ser Gly Ala
    4595             4600              4605

Gly Ala  Gly Ser Gly Ala Gly  Ala Gly Ser Gly  Ala  Gly Ala Gly
```

-continued

```
                4610               4615                4620

Ser Gly Ala Gly Ala Gly Ser Gly Ala Gly Ser Gly Ala
        4625               4630                4635

Gly Ala Gly Ser Gly Ala Gly Ala Gly Ser Gly Ala Gly
        4640               4645                4650

Tyr Gly Ala Gly Tyr Gly Ala Gly Ala Gly Tyr Gly Ala
        4655               4660                4665

Gly Ala Gly Val Gly Tyr Gly Ala Gly Ala Gly Tyr Gly
        4670               4675                4680

Ala Gly Ala Gly Ser Gly Ala Gly Ser Gly Ala Gly Ser
        4685               4690                4695

Gly Ser Gly Ala Gly Ala Gly Ser Gly Ser Gly Ala Gly Ser Gly
        4700               4705                4710

Ala Gly Ala Gly Ser Gly Ala Gly Ala Gly Ser Gly Ala Gly Ala
        4715               4720                4725

Gly Ser Gly Ala Gly Ala Gly Ser Gly Ala Gly Ala Gly Ser Gly
        4730               4735                4740

Ala Gly Ala Gly Ser Gly Ala Gly Ala Gly Tyr Gly Ala Gly Tyr
        4745               4750                4755

Gly Ile Gly Val Gly Ala Gly Tyr Gly Ala Gly Ala Gly Val Gly
        4760               4765                4770

Tyr Gly Ala Gly Ala Gly Ala Gly Tyr Gly Ala Gly Ala Gly Ser
        4775               4780                4785

Gly Ala Ala Ser Gly Ala Gly Ala Gly Ser Gly Ala Gly Ala Gly
        4790               4795                4800

Ser Gly Ala Gly Ala Gly Ser Gly Ala Gly Ala Gly Ser Gly Ala
        4805               4810                4815

Gly Ala Gly Ser Gly Ala Gly Ala Gly Ser Gly Ala Gly Ala Gly
        4820               4825                4830

Ser Gly Ala Gly Ala Gly Ser Gly Ala Gly Ala Gly Ser Gly Ala
        4835               4840                4845

Gly Ala Gly Tyr Gly Ala Gly Ala Gly Val Gly Tyr Gly Ala Gly
        4850               4855                4860

Ala Gly Ser Gly Ala Ala Ser Gly Ala Gly Ala Gly Ser Gly Ala
        4865               4870                4875

Gly Ala Gly Ser Gly Ala Gly Ala Gly Ser Gly Ala Gly Ala Gly
        4880               4885                4890

Ser Gly Ala Gly Ala Gly Ser Gly Ala Gly Ala Gly Ser Gly Ala
        4895               4900                4905

Gly Ala Gly Ser Gly Ala Gly Ser Gly Ala Gly Ala Gly Ser Gly
        4910               4915                4920

Ala Gly Ala Gly Tyr Gly Ala Gly Tyr Gly Ala Gly Val Gly Ala
        4925               4930                4935

Gly Tyr Gly Ala Gly Ala Gly Tyr Gly Ala Gly Tyr Gly Val Gly
        4940               4945                4950

Ala Gly Ala Gly Tyr Gly Ala Gly Ala Gly Ser Gly Ala Gly Ser
        4955               4960                4965

Gly Ala Gly Ala Gly Ser Gly Ala Gly Ala Gly Ser Gly Ala Gly
        4970               4975                4980

Ala Gly Ser Gly Ala Gly Ala Gly Ser Gly Ala Gly Ala Gly Ser
        4985               4990                4995

Gly Ala Gly Ser Gly Ala Gly Ala Gly Tyr Gly Ala Gly Ala Gly
        5000               5005                5010
```

Ala Gly Tyr Gly Ala Gly Ala Gly Ala Gly Tyr Gly Ala Gly Ala
        5015                5020                5025

Gly Ser Gly Ala Ala Ser Gly Ala Gly Ala Gly Ala Gly Ala Gly
        5030                5035                5040

Ser Gly Ala Gly Ala Gly Ser Gly Ala Gly Ala Gly Ser Gly Ala
        5045                5050                5055

Gly Ser Gly Ala Gly Ala Gly Ser Gly Ala Gly Ala Gly Tyr Gly
        5060                5065                5070

Ala Gly Ala Gly Ser Gly Ala Ala Ser Gly Ala Gly Ala Gly Ser
        5075                5080                5085

Gly Ala Gly Ala Gly Ala Gly Ala Gly Ala Gly Ala Gly Ser Gly
        5090                5095                5100

Ala Gly Ala Gly Ser Gly Ala Gly Ala Gly Tyr Gly Ala Gly Ala
        5105                5110                5115

Gly Ser Gly Ala Ala Ser Gly Ala Gly Ala Gly Ala Gly Ala Gly
        5120                5125                5130

Thr Gly Ser Ser Gly Phe Gly Pro Tyr Val Ala Asn Gly Gly Tyr
        5135                5140                5145

Ser Arg Arg Glu Gly Tyr Glu Tyr Ala Trp Ser Ser Lys Ser Asp
        5150                5155                5160

Phe Glu Thr Gly Ser Gly Ala Ala Ser Gly Ala Gly Ala Gly Ala
        5165                5170                5175

Gly Ser Gly Ala Gly Ala Gly Ser Gly Ala Gly Ala Gly Ser Gly
        5180                5185                5190

Ala Gly Ala Gly Ser Gly Ala Gly Ala Gly Gly Ser Val Ser Tyr
        5195                5200                5205

Gly Ala Gly Arg Gly Tyr Gly Gln Gly Ala Gly Ser Ala Ala Ser
        5210                5215                5220

Ser Val Ser Ser Ala Ser Ser Arg Ser Tyr Asp Tyr Ser Arg Arg
        5225                5230                5235

Asn Val Arg Lys Asn Cys Gly Ile Pro Arg Arg Gln Leu Val Val
        5240                5245                5250

Lys Phe Arg Ala Leu Pro Cys Val Asn Cys
        5255                5260

<210> SEQ ID NO 11
<211> LENGTH: 262
<212> TYPE: PRT
<213> ORGANISM: Bombyx mori

<400> SEQUENCE: 11

Met Lys Pro Ile Phe Leu Val Leu Leu Val Ala Thr Ser Ala Tyr Ala
1               5                   10                  15

Ala Pro Ser Val Thr Ile Asn Gln Tyr Ser Asp Asn Glu Ile Pro Arg
                20                  25                  30

Asp Ile Asp Asp Gly Lys Ala Ser Ser Val Ile Ser Arg Arg Trp Asp
            35                  40                  45

Tyr Val Asp Asp Thr Asp Lys Ser Ile Ala Ile Leu Asn Val Gln Glu
        50                  55                  60

Ile Leu Lys Asp Met Ala Ser Gln Gly Asp Tyr Ala Ser Gln Ala Ser
65                  70                  75                  80

Ala Val Ala Gln Thr Ala Gly Ile Ile Ala His Leu Ser Ala Gly Ile
                85                  90                  95

Pro Gly Asp Ala Cys Ala Ala Ala Asn Val Ile Asn Ser Tyr Thr Asp

```
                    100                 105                 110
Gly Val Arg Ser Gly Asn Phe Ala Gly Phe Arg Gln Ser Leu Gly Pro
            115                 120                 125

Phe Phe Gly His Val Gly Gln Asn Leu Asn Leu Ile Asn Gln Leu Val
        130                 135                 140

Ile Asn Pro Gly Gln Leu Arg Tyr Ser Val Gly Pro Ala Leu Gly Cys
145                 150                 155                 160

Ala Gly Gly Arg Ile Tyr Asp Phe Glu Ala Ala Trp Asp Ala Ile
            165                 170                 175

Leu Ala Ser Ser Asp Ser Ser Phe Leu Asn Glu Glu Tyr Cys Ile Val
                180                 185                 190

Lys Arg Leu Tyr Asn Ser Arg Asn Ser Gln Ser Asn Asn Ile Ala Ala
            195                 200                 205

Tyr Ile Thr Ala His Leu Leu Pro Pro Val Ala Gln Val Phe His Gln
210                 215                 220

Ser Ala Gly Ser Ile Thr Asp Leu Leu Arg Gly Val Gly Asn Gly Asn
225                 230                 235                 240

Asp Ala Thr Gly Leu Val Ala Asn Ala Gln Arg Tyr Ile Ala Gln Ala
            245                 250                 255

Ala Ser Gln Val His Val
            260

<210> SEQ ID NO 12
<211> LENGTH: 19
<212> TYPE: DNA
<213> ORGANISM: Artificial Sequence
<220> FEATURE:
<223> OTHER INFORMATION: Target site of gRNA FibH_1

<400> SEQUENCE: 12
gctaataggt agggaaaac                                                19

<210> SEQ ID NO 13
<211> LENGTH: 19
<212> TYPE: DNA
<213> ORGANISM: Artificial Sequence
<220> FEATURE:
<223> OTHER INFORMATION: Target site of gRNA FibH_2

<400> SEQUENCE: 13
atgtgaccat aaaatctcg                                                19

<210> SEQ ID NO 14
<211> LENGTH: 20
<212> TYPE: DNA
<213> ORGANISM: Artificial Sequence
<220> FEATURE:
<223> OTHER INFORMATION: Target site of gRNA FibH_3

<400> SEQUENCE: 14
aactcgttcc agatcagcgc                                               20

<210> SEQ ID NO 15
<211> LENGTH: 70
<212> TYPE: DNA
<213> ORGANISM: Artificial Sequence
<220> FEATURE:
<223> OTHER INFORMATION: Primer for Gibson Assembly

<400> SEQUENCE: 15
gctagaagca gcagccgcat ctacaccggt gatatcgcct cctccgagaa cgtcatcacc   60
```

-continued

```
gagttcatgc                                                             70

<210> SEQ ID NO 16
<211> LENGTH: 70
<212> TYPE: DNA
<213> ORGANISM: Artificial Sequence
<220> FEATURE:
<223> OTHER INFORMATION: Primer for Gibson Assembly

<400> SEQUENCE: 16
ttggacacgg tctggctgat gcttccggag tcgaccttgt acagctcgtc catgccgaga       60
gtgatcccgg                                                             70

<210> SEQ ID NO 17
<211> LENGTH: 68
<212> TYPE: DNA
<213> ORGANISM: Artificial Sequence
<220> FEATURE:
<223> OTHER INFORMATION: Primer for Gibson Assembly (HC-Gamma-F)

<400> SEQUENCE: 17
tcaacaatca tcctgcagca aaccggtgat atcgcctcct ccgagaacgt catcaccgag       60
ttcatgcg                                                               68

<210> SEQ ID NO 18
<211> LENGTH: 70
<212> TYPE: DNA
<213> ORGANISM: Artificial Sequence
<220> FEATURE:
<223> OTHER INFORMATION: Primer for Gibson Assembly (HC-Gamma-R)

<400> SEQUENCE: 18
tatgacacgc tgctgtgtga agctccggag tcgaccttgt acagctcgtc catgccgaga       60
gtgatcccgg                                                             70

<210> SEQ ID NO 19
<211> LENGTH: 73
<212> TYPE: DNA
<213> ORGANISM: Artificial Sequence
<220> FEATURE:
<223> OTHER INFORMATION: Primer for Gibson Assembly (LC-GA-alpha-F)

<400> SEQUENCE: 19
cagctagaag cagcagccgc atctacaccg gtgatatcgc ggatcctgcg accggcttag       60
ttgctaatgc tca                                                         73

<210> SEQ ID NO 20
<211> LENGTH: 72
<212> TYPE: DNA
<213> ORGANISM: Artificial Sequence
<220> FEATURE:
<223> OTHER INFORMATION: Primer for Gibson Assembly (LC-GA-alpha-R)

<400> SEQUENCE: 20
gtgtagcttt tggacacggt ctggctgatg cttccggagt cgacaagctt cttgtacagc       60
tcgtccatgc cg                                                          72

<210> SEQ ID NO 21
<211> LENGTH: 72
<212> TYPE: DNA
<213> ORGANISM: Artificial Sequence
<220> FEATURE:
```

<223> OTHER INFORMATION: Primer for Gibson Assembly (LC-GA-Gamma-F)

<400> SEQUENCE: 21
tcaacaatca tcctgcagca aaccggtgat atcgcggatc ctgcgaccgg cttagttgct    60
aatgctcaaa ga    72

<210> SEQ ID NO 22
<211> LENGTH: 70
<212> TYPE: DNA
<213> ORGANISM: Artificial Sequence
<220> FEATURE:
<223> OTHER INFORMATION: Primer for Gibson Assembly (LC-GA-Gamma-R)

<400> SEQUENCE: 22
tatgacacgc tgctgtgtga agctccggag tcgacaagct tcttgtacag ctcgtccatg    60
ccgagagtga    70

<210> SEQ ID NO 23
<211> LENGTH: 36
<212> TYPE: DNA
<213> ORGANISM: Artificial Sequence
<220> FEATURE:
<223> OTHER INFORMATION: Primer for PCR (eGFP-SalI-F; First - Forward)

<400> SEQUENCE: 23
atagtcgacg tgagcaaggg cgaggagctg ttcacc    36

<210> SEQ ID NO 24
<211> LENGTH: 34
<212> TYPE: DNA
<213> ORGANISM: Artificial Sequence
<220> FEATURE:
<223> OTHER INFORMATION: Primer for PCR (eGFP-HindIII-R; First -
      Reverse)

<400> SEQUENCE: 24
gcaagcttct tgtacagctc gtccatgccg agag    34

<210> SEQ ID NO 25
<211> LENGTH: 30
<212> TYPE: DNA
<213> ORGANISM: Artificial Sequence
<220> FEATURE:
<223> OTHER INFORMATION: Primer for PCR (Dsred-BamHI; First - Forward)

<400> SEQUENCE: 25
ataggatccc gcctcctccg agaacgtcat    30

<210> SEQ ID NO 26
<211> LENGTH: 28
<212> TYPE: DNA
<213> ORGANISM: Artificial Sequence
<220> FEATURE:
<223> OTHER INFORMATION: Primer for PCR (Dsred-XbaI; First - Reverse)

<400> SEQUENCE: 26
taatctagac aggaacaggt ggtggcgg    28

<210> SEQ ID NO 27
<211> LENGTH: 20
<212> TYPE: DNA
<213> ORGANISM: Artificial Sequence
<220> FEATURE:
<223> OTHER INFORMATION: Primer for PCR (HC_DsRed_1_F; Secondary -
      Forward)

```
<400> SEQUENCE: 27
cacgagttcg agatcgaggg                                              20

<210> SEQ ID NO 28
<211> LENGTH: 20
<212> TYPE: DNA
<213> ORGANISM: Artificial Sequence
<220> FEATURE:
<223> OTHER INFORMATION: Primer for PCR (HC_DsRed_1_R; Secondary -
      Reverse)

<400> SEQUENCE: 28
gcgtccacgt agtagtagcc                                              20

<210> SEQ ID NO 29
<211> LENGTH: 20
<212> TYPE: DNA
<213> ORGANISM: Artificial Sequence
<220> FEATURE:
<223> OTHER INFORMATION: Primer for PCR (HC_DsRed_2_F; Secondary -
      Forward)

<400> SEQUENCE: 29
ccgacatccc cgactacaag                                              20

<210> SEQ ID NO 30
<211> LENGTH: 20
<212> TYPE: DNA
<213> ORGANISM: Artificial Sequence
<220> FEATURE:
<223> OTHER INFORMATION: Primer for PCR (HC_DsRed_2_R; Secondary -
      Reverse)

<400> SEQUENCE: 30
acgccgatga acttcacctt                                              20

<210> SEQ ID NO 31
<211> LENGTH: 20
<212> TYPE: DNA
<213> ORGANISM: Artificial Sequence
<220> FEATURE:
<223> OTHER INFORMATION: Primer for PCR (FibH62454-F; 5' First -
      Forward0

<400> SEQUENCE: 31
ttgtgatctt gtgctgcgct                                              20

<210> SEQ ID NO 32
<211> LENGTH: 19
<212> TYPE: DNA
<213> ORGANISM: Artificial Sequence
<220> FEATURE:
<223> OTHER INFORMATION: Primer for PCR (H1-R; 5' First - Reverse)

<400> SEQUENCE: 32
cagggtcagc ttgccgtag                                               19

<210> SEQ ID NO 33
<211> LENGTH: 20
<212> TYPE: DNA
<213> ORGANISM: Artificial Sequence
<220> FEATURE:
<223> OTHER INFORMATION: Primer for PCR (FibH62737-F; 5' Secondary -
      Forward)

<400> SEQUENCE: 33
```
caccggtaaa tcagcattgc                                                20

<210> SEQ ID NO 34
<211> LENGTH: 20
<212> TYPE: DNA
<213> ORGANISM: Artificial Sequence
<220> FEATURE:
<223> OTHER INFORMATION: Primer for PCR (FibH-donor-R; 5' Secondary - Reverse)

<400> SEQUENCE: 34
cgactgcagc actagtgctg                                                20

<210> SEQ ID NO 35
<211> LENGTH: 20
<212> TYPE: DNA
<213> ORGANISM: Artificial Sequence
<220> FEATURE:
<223> OTHER INFORMATION: Primer for PCR (PSK-F; 3' First - Forward)

<400> SEQUENCE: 35
gggcgatcgg tgcgggcctc                                                20

<210> SEQ ID NO 36
<211> LENGTH: 20
<212> TYPE: DNA
<213> ORGANISM: Artificial Sequence
<220> FEATURE:
<223> OTHER INFORMATION: Primer for PCR (FibH63746-R; 3' First - Reverse)

<400> SEQUENCE: 36
tgagcaacag taccatcgga                                                20

<210> SEQ ID NO 37
<211> LENGTH: 20
<212> TYPE: DNA
<213> ORGANISM: Artificial Sequence
<220> FEATURE:
<223> OTHER INFORMATION: Primer for PCR (PSK-F2; 3' Secondary - Forward)

<400> SEQUENCE: 37
tacgactcac tatagggcga                                                20

<210> SEQ ID NO 38
<211> LENGTH: 20
<212> TYPE: DNA
<213> ORGANISM: Artificial Sequence
<220> FEATURE:
<223> OTHER INFORMATION: Primer for PCR (FibH63575-R; 3' Secondary - Reverse)

<400> SEQUENCE: 38
tcgataactg ccccagatgc                                                20

<210> SEQ ID NO 39
<211> LENGTH: 28
<212> TYPE: DNA
<213> ORGANISM: Artificial Sequence
<220> FEATURE:
<223> OTHER INFORMATION: Primer for PCR (LC-NHEJ-LJ13201-F; 5' First - Forward)

<400> SEQUENCE: 39
aagatggatc aaactgcaca cggtgtgc                                       28

```
<210> SEQ ID NO 40
<211> LENGTH: 28
<212> TYPE: DNA
<213> ORGANISM: Artificial Sequence
<220> FEATURE:
<223> OTHER INFORMATION: Primer for PCR (LC-NHEJ-LJ13389-F; 5'
      Secondary - Forward)

<400> SEQUENCE: 40
aagagattgt acaactctcg caacagcc                                      28

<210> SEQ ID NO 41
<211> LENGTH: 21
<212> TYPE: DNA
<213> ORGANISM: Artificial Sequence
<220> FEATURE:
<223> OTHER INFORMATION: Primer for PCR (LJ-R1; 5' Secondary - Reverse)

<400> SEQUENCE: 41
gtaaacggcc acaagttcag c                                             21

<210> SEQ ID NO 42
<211> LENGTH: 20
<212> TYPE: DNA
<213> ORGANISM: Artificial Sequence
<220> FEATURE:
<223> OTHER INFORMATION: Primer for PCR (LS-R; 5' First - Reverse)

<400> SEQUENCE: 42
tacggcaagc tgaccctgaa                                               20

<210> SEQ ID NO 43
<211> LENGTH: 20
<212> TYPE: DNA
<213> ORGANISM: Artificial Sequence
<220> FEATURE:
<223> OTHER INFORMATION: Primer for PCR (PSK-F; 3' First - Forward)

<400> SEQUENCE: 43
gggcgatcgg tgcgggcctc                                               20

<210> SEQ ID NO 44
<211> LENGTH: 20
<212> TYPE: DNA
<213> ORGANISM: Artificial Sequence
<220> FEATURE:
<223> OTHER INFORMATION: Primer for PCR (PSK-F2; 3' Secondary - Forward)

<400> SEQUENCE: 44
tacgactcac tatagggcga                                               20

<210> SEQ ID NO 45
<211> LENGTH: 20
<212> TYPE: DNA
<213> ORGANISM: Artificial Sequence
<220> FEATURE:
<223> OTHER INFORMATION: Primer for PCR (LC-NHEJ-RJ14589-R; 3'
      Secondary - Reverse)

<400> SEQUENCE: 45
ccaatccacc gtctttgggt                                               20

<210> SEQ ID NO 46
<211> LENGTH: 24
<212> TYPE: DNA
<213> ORGANISM: Artificial Sequence
```

```
<220> FEATURE:
<223> OTHER INFORMATION: Primer for PCR (Sac1-14600-R-R; 3' First -
      Reverse)

<400> SEQUENCE: 46
gacggtggat tggacagtgg gtac                                          24

<210> SEQ ID NO 47
<211> LENGTH: 1950
<212> TYPE: DNA
<213> ORGANISM: Artificial Sequence
<220> FEATURE:
<223> OTHER INFORMATION: DNA sequence of hagfish alpha with AgeI, BspEI,
      SalI and EcoRV

<400> SEQUENCE: 47
gtcgactccg gaagcatcag ccagaccgtg tccaaaagct acacaaaaag cgtgtcaaga     60
ggtggccaag gcgtgtcata ctcacaatca tcatcacaca aagtcggagg tggaagcgtc    120
agatacggaa caacatactc aagcggagga atcagcagag tgctgggatt ccaaggtggt    180
gctggtggtg cagcttcagc tggattcgga ggatcagtcg gtggatcagg actgtcaaga    240
gtgctcggag gttcaatggt gtcaggatac agatctggaa tgggtgtcgg aggactgtct    300
ctgtctggaa cagctggact gcctgtgtca ctgagaggtg tcggtgctgg aaaagctctg    360
cacgctatca aagcgcttt cagaacaaga gtcggtggtc ctggaacatc agttggagga    420
tacggtgtca actacagctt cctgccttca acagctggtc cttcattcgg tggacctttc    480
ggaggaccat ttggaggccc gttcggaggt cctctcggac tggatatat cgaccctgct    540 acactgcctt cacctgacac agtgcaacac accagaatcc gcgaaaaaca agacctgcag    600
accctgaaca ccaagttcgc taacctggtg gaccaagtgc gcacactgga caacacaaac    660
gctatcctga agcccagat cagcatgatc acatcaccta gcgacacacc tgaaggacct    720
gtgaacactg ctgtggtggc ttcaacagtg acagctacct acaacgctca aatcgaggac    780
ctgagaacca caaacactgc tctgcactca gaaatcgacc acctgacaac catcatcaac    840
gacatcacca cgaagtacga ggaacaggtg gaagtgacaa gaacactgga aaccgactgg    900
aacaccaaca aggacaacat cgacaacacc tacctgacaa tcgtggacct ccagacaaaa    960
gtgcaaggac tggacgaaca gatcaacacc accaaacaaa tctacaacgc cagagtgcgc   1020
gaagtgcaag ctgctgtgac aggtggacct acagctgctt actcaatcag agtggacaac   1080
acacaccagg ctatcgacct gactacaagc ctgcaagaaa tgaagaccca ctacgaagtg   1140
ctggctacca aaagcagaga agaagctttc acacaggtcc agcctcgcat ccaagaaatg   1200
gctgtgactg tgcaggctgg tcctcaagct atcatccagg ctaaagaaca gatccacgtg   1260
ttcaagctgc aaatcgacag cgtgcacaga gagattgaca gactgcacag aaagaacacc   1320
gacgtggaac gcgaaatcac cgtgatcgaa acaaacatcc acacgcagag cgacgagtgg   1380
actaacaaca tcaactcact gaaagtggac ctggaagtca tcaagaagca gatcacacaa   1440
tacgctcgcg actaccaaga cctcctggct acaaaaatga gcctggacgt ggaaatcgct   1500
gcctacaaaa aactgctgga cagcgaagaa actcgcatct cacacggtgg tggaatcaca   1560
atcacaacaa cgctggaac attcccaggt ggactgtcag ctgctcctgg tgtggtgct    1620 tcatacgcta tggttccagc tggtgtcggc ggagttggat tggctggtgt tggtggttac   1680
ggattcagat caatgggagg tggtggcgga gtcggatatg gtgctggcgg aggtggcgtt   1740
ggatatggcg ttggtggtgg atttggaggt ggcatggaa tgtcaatgag cagaatgtct   1800
```

| | |
|---|---|
| atgggagctg ctgtcggtgg tggttcttac ggatcaggat ctggatactc tggtggtttc | 1860 |
| ggactgtcat catcaagagc tggatacagc gctagcagaa agtcatactc ttcagctaga | 1920 |
| agcagcagcc gcatctacac cggtgatatc | 1950 |

<210> SEQ ID NO 48
<211> LENGTH: 1830
<212> TYPE: DNA
<213> ORGANISM: Artificial Sequence
<220> FEATURE:
<223> OTHER INFORMATION: DNA sequence of hagfish gamma with AgeI, BspEI, SalI and EcoRV

<400> SEQUENCE: 48

| | |
|---|---|
| gtcgactccg gagcttcaca cagcagcgtg tcatacagat cagtcagaac aggtggaacc | 60 |
| agcgctatga tcggatcatc aggatacggt ggatcaagct catcaagagc tatgggactc | 120 |
| ggaatgggag ctgctggact gtcaatgggt ggtggatcat tcagagtggg atcagctgga | 180 |
| atcggaggaa tggaatctc atctggtatt ggaggcatgg gtatcagctc aagagctggt | 240 |
| ggaatgtctg cttacggtgg tgctgctagc ggaggtgctg gtggattcgt ttcaggtggt | 300 |
| gtccctatgc tcggatatgg tggtggcgct ggtggtttca tcggtggtgt ctcacctgga | 360 |
| atcatggctt caccagcttt cacagctggt agagctatca catctgctgg aatgagcgga | 420 |
| gtcgtgggaa cattaggacc tgctggtggc atggtgcctt cactggtgtc aagagatgaa | 480 |
| gtgaaaaaca tcctgggcac cctgaaccag agactggctt catacgtgga caaagtgcgc | 540 |
| cagctgacaa tcgagaacga aaccatggaa gaggaactga aaaacctgac aggcggagtg | 600 |
| cctatgtcac ctgactcaac agtgaacctg gaaaacgtgg aaacccaagt gaccgaaatg | 660 |
| ctgaccgaag tgtctaacct gacactgaaa agagtgcgcc tggaaatcga cgtggaccac | 720 |
| ctgagagcta cagctgacga aatcaagtcg aagtacgaat cgaactggg agtgcgcatg | 780 |
| cagctggaaa cagacattgc taacatgaag cgcgacctgg aagctgctaa cgacatgaga | 840 |
| gtggacctgg acagcaaatt caacttcctc accgaagaac tgaccttcca gcgcaaaaca | 900 |
| cagatggaag aactcaacac cctgaaacag cagttcggta gactgggacc tgtgcaaaca | 960 |
| tcagtgatcg agctggacaa cgtgaaaagc gtgaacctga ctgacgctct gaacgtgatg | 1020 |
| cgcgaagaat accaacaggt ggtcaccaag aacgtgcaag aagctgaaac ctactgcaag | 1080 |
| atgcagatcg accaaatcca gggaatcagc acacagacaa ccgaacaaat cagcatcctg | 1140 |
| gacaaagaga tcaacacgct cgaaaaagaa ctgcagccgc tgaacgtgga ataccaaaga | 1200 |
| ctgctgacaa cctaccagac actgggagac agactgacag acctgcagaa cagagaatca | 1260 |
| atcgacctgg tgcagttcca gaacacatac acccgctacg aacaagaaat cgaaggcaac | 1320 |
| caggtggacc tgcaaagaca actggtcaca taccaacaac tgctcgacgt gaaaacagct | 1380 |
| ctggacgctg aaatcgccac ctacaaaaaa ctgctggaag gccaagaact gatggtccga | 1440 |
| acagctatgg ctgacgactt cgctcacgct acagtcgtca gatctggaac actcggaggc | 1500 |
| gcttcatcat catcagtcgg ttacggtgct tcaagcacaa cactgggtgc tatctctggt | 1560 |
| ggatactcta caggtggtgg tgcttcatac tcagctggtg ctggcggagc ttcttattct | 1620 |
| gctggtgccg gtggtgcctc ttacggtgtt ggtggtggtt actctggtgg tagctcagct | 1680 |
| atgatggaag gatcatcatc tggtggccac tcaatgtaca gctcgtctag catgaagaga | 1740 |
| agcagcagca aatcagcttc agctagcgct ggcggttacg gaacatcagg acacgactca | 1800 |
| acaatcatcc tgcagcaaac cggtgatatc | 1830 |